US009238061B2

(12) United States Patent
Blumenfeld

(10) Patent No.: US 9,238,061 B2
(45) Date of Patent: *Jan. 19, 2016

(54) BOTULINUM TOXIN TREATMENT OF ANXIETY AND BIPOLAR DISORDERS

(71) Applicant: Allergan, Inc., Irvine, CA (US)

(72) Inventor: Andrew M. Blumenfeld, Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/086,086

(22) Filed: Nov. 21, 2013

(65) Prior Publication Data

US 2014/0099298 A1    Apr. 10, 2014

Related U.S. Application Data

(63) Continuation of application No. 13/053,583, filed on Mar. 22, 2011, now Pat. No. 8,617,572, which is a continuation-in-part of application No. 10/964,898, filed on Oct. 12, 2004, now Pat. No. 8,734,810.

(60) Provisional application No. 60/515,362, filed on Oct. 29, 2003, provisional application No. 60/556,150, filed on Mar. 24, 2004, provisional application No. 60/574,957, filed on May 26, 2004.

(51) Int. Cl.
*A61K 38/48*    (2006.01)
*A61K 9/00*    (2006.01)

(52) U.S. Cl.
CPC ........... *A61K 38/4893* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 4,883,666 A | 11/1989 | Sabel et al. | 424/422 |
| 5,427,291 A | 6/1995 | Smith | |
| 5,674,205 A | 10/1997 | Pasricha et al. | |
| 5,978,702 A | 11/1999 | Ward et al. | |
| 6,094,598 A | 7/2000 | Elsberry et al. | 607/116 |
| 6,113,915 A | 9/2000 | Aoki et al. | |
| 6,143,306 A | 11/2000 | Donovan | |
| 6,265,379 B1 | 7/2001 | Donovan | |
| 6,290,961 B1 | 9/2001 | Aoki et al. | |
| 6,306,403 B1 | 10/2001 | Donovan | |
| 6,328,977 B1 | 12/2001 | Donovan | |
| 6,358,513 B1 | 3/2002 | Voet et al. | |
| 6,365,164 B1 | 4/2002 | Schmidt | |
| 6,395,277 B1 | 5/2002 | Graham | |
| 6,620,415 B2 | 9/2003 | Donovan | 424/239.1 |
| 6,689,816 B2 | 2/2004 | Fogel | 514/702 |
| 6,955,813 B2 | 10/2005 | Brooks et al. | 424/239.1 |
| 7,357,934 B2 | 4/2008 | Donovan et al. | |
| 7,361,358 B2 | 4/2008 | Aoki et al. | |
| 7,374,769 B2 | 5/2008 | Aoki et al. | |
| 7,758,872 B1 | 7/2010 | Finzi | |
| 2001/0012828 A1 | 8/2001 | Aoki et al. | 514/2 |
| 2001/0053370 A1 | 12/2001 | Donovan | 424/239.1 |
| 2002/0176872 A1 | 11/2002 | Aoki et al. | 424/247.1 |
| 2002/0192239 A1 | 12/2002 | Borodic et al. | |
| 2003/0054975 A1 | 3/2003 | Voet | 514/2 |
| 2003/0234727 A1 | 12/2003 | Perlman | 340/573.1 |
| 2004/0138097 A1 | 7/2004 | Guyuron | |
| 2004/0157926 A1 | 8/2004 | Heresco-Levy et al. | 514/561 |
| 2006/0171963 A1 | 8/2006 | Blumenfeld | |
| 2006/0286127 A1 | 12/2006 | Van Schaack et al. | 424/239.1 |
| 2008/0160121 A1 | 7/2008 | Donovan et al. | |
| 2008/0279895 A1 | 11/2008 | Blumenfeld | |

FOREIGN PATENT DOCUMENTS

| | | | | |
|---|---|---|---|---|
| DE | 101 50 415 A1 | 10/2001 | | A61K 35/70 |
| DE | 10150415 | 5/2003 | | |
| EP | 0 605 501 B1 | 9/1992 | | |
| WO | WO 95/17904 | 7/1995 | | |
| WO | WO95-30431 | 11/1995 | | |
| WO | WO 97/20579 | 6/1997 | | |
| WO | WO 00/07652 | 2/2000 | | |
| WO | WO 00/15245 | 3/2000 | | A61K 38/16 |
| WO | WO01-26736 | 4/2001 | | |
| WO | WO01-95924 | 12/2001 | | |
| WO | WO 03/094955 | 4/2003 | | A61K 38/48 |
| WO | WO03-096955 | 11/2003 | | |

OTHER PUBLICATIONS

Hirschfeld. The Comorbidity of Major Depression and Anxiety Disorders: Recognition and Management in Primary Care. Primary Care Companion to the Journal of Clinical Psychiatry. 2001;3(6):244-254.*

Geddes. Bipolar disorder. Evid Based Ment Health. Nov. 2003;6(4):101-2.*

Amy M. Lang, Botulinum Toxin Type A Therapy in Chronic Pain Disorders, Archives of Physical Medicine and Rehabilitation, Mar. 2003, S69-S73, 84 (Suppl 1), US.

(Continued)

*Primary Examiner* — Gregory S Emch
(74) *Attorney, Agent, or Firm* — Brigitte C. Phan; Ted A. Chan

(57) ABSTRACT

Methods for preventing or treating depression including a depression mediated by the thalamus. Depression, including a thalamically mediated depression, can be treated by peripheral administration of a botulinum toxin to or to the vicinity of a trigeminal sensory nerve, thereby preventing or treating the depression.

20 Claims, 2 Drawing Sheets

(56) References Cited

OTHER PUBLICATIONS

Aoki, K. Roger et al, Mechanisms of the antinociceptive effect of subcutaneous Botox®: inhibition of peripheral and central nociceptive processing, Cephalalgia, Sep. 2003, 649 (abstract), 23(7), US.
Aoki, Kei Roger, Evidence from Antinociceptive Activity of Botulinum Toxin Type A in pain Management Headache, 2003, S9-S15, 43 (Suppl 1).
Aoki, Roger Kei et al, Mechanisms of the Antinociceptive Effect of Subcutaneous Botox Inhibition of Peripheral and Central Nociceptive Processing, Cephalalgia, 2003, 649 (1 Page), 23.
Brem, Henry et al, Placebo-Controlled Trial of Safety and Efficacy of Intraoperative Controlled Delivery by Biodegradable Polymers of Chemotherapy for Recurrent Gliomas, The Lancet, 1995, 1008-1012, 345.
Bruce D. Nicholson, Evaluation and Treatment of Central Pain Syndromes, Neurology, Mar. 2004, 30-36, 62 (Suppl. 2), US.
Cui, M, Deutsche Gesellschaft fur experimentelle und klinische Pharmakologie und Toxikologie, Springer, 2002, 48 pages, DE.
Durham, Paul L., Regulation of Calcitonin Gene-Related Peptide Scretion from Trigeminal Nerve Cells by Botulinum Toxin Type A: Implications for Migraine Therapy, 2004, pp. 35-43, 44.
Fung, Lawrence et al, Pharmacokinetics of Interstitial Delivery of Carmustine, 4-Hydroperoxycyclophosphamide, and Paclitaxel From a Biodegradable Polymer Implant in the Monkey Brain, Cancer Research, Feb. 15, 1998, 672-684, 58.
Gary E. Bordic, et al., The Use of Botulinum Toxin for the Treatment of Chronic Facial Pain, The Journal of Pain, 02/20002, 22-27, 3 (1), US.
Gerald B. Dermer, Another Anniversary for the War on Cancer, Bio/Technology, Mar. 12, 1994, 1 page (starting at 320), 12.
Graham V. Goddard, A Permanent Change in Brain Function Resultingfrom Daily Electrical Stimulation, 1969.
Guyuron, Bahman et al, Surgical Treatment of Migraine Headaches, Plast Reconstr Surg, 2002, 2183-2189, 109.
Hayrunnisa Bolay, et al., Intrinsic Brain Activity Triggers Trigeminal Meningeal Afferents in a Migraine Model, Nature Medicine, Feb. 2002, 136-142, 8 (2), US.
Jankovic, J., Pharmacology and Histology of the TherapeuticApplication of Botulinum Toxin, 1994, 119-157, 25.
K. Roger Aoki, Evidence for Antinociceptive Activity of Botulinum Toxin Type A in Pain Management, Headache 2003, Aug. 2003, S9-S15, 43 (Supp 1), US.
Kouichi Kurata, et al., Complete Remission of Neuroleptic-Induced Meige's Syndrome by Botulinum Toxin Treatment: A Case Report, The Japanese Journal of Psychiatry and Neurology, 1993, 115-119, 47, US.
Marjan Jahanshahi, Psychological functioning before and after treatment of torticollis with botulinum toxin, 1992.
Marwan N. Sabbagh, Drug Development for Alzheimer's Disease: Where Are We Now and Where Are We Headed?, The American Journal of Geriatric Pharmacotherapy, Jun. 2009, 167-185, 7 (3), US.
Noble A. Endicott, Psychophysiological correlates of 'bipolarity', Journal of Affective Disorders, 1989, 47-56, 17.
R. Laskawi, et al., Essential blepharospasm and botulinum toxin An electrophysiologic study, HNO, Jan. 1990, 29-32, 38, DE.
Raymond G. Auger, Hemimasticatory Spasm: Clinical and Electrophysiologic Observations, Neurology 1992, Dec. 1992, 2263-2266, 42, US.
Robert M. Post, Shared m.echanisDls in aiffective illness, epilepsy, and :migraine, 1994.
Sheftell, Fred et al, Migraine and Psychiatric Comorbidity: From Theory and Hypotheses to Clinical Application, Headache, 2002, 934-944, 242.
Thomas Murry, Spasmodic Dysphonia, Mar. 1994.
Thuerauf, N. et al, Dose-Dependent Steroselective Activation of the Trigeminal Sensory System by Nicotine in Man, Psychopharmacology, 1999, 236-243, 142.

Pierson, S., et al., "Botulinum Toxin A in the Treatment of Spasticity: Functional Implication and Patent Selection" Arch Phys Med Rehab Jul. 1996; 77(7):717-21.
U.S. Appl. No. 10/423,384, filed Apr. 25, 2003, Ackerman, Alan H.
U.S. Appl. No. 10/423,778, filed Apr. 25, 2003, Ackerman, Alan H.
U.S. Appl. No. 10/424,009, filed Apr. 25, 2003, Ackerman, Alan H.
U.S. Appl. No. 10/424,050, filed Apr. 25, 2003, Ackerman, Alan H.
Aguilera, Jose et al., *Stereotaxic Injection of Tetanus Toxin in Rat Central Nervous System Causes Alteration in Normal Levels of Monoamines*, Journal of Neurochemistry, vol. 56, No. 3, 1991, pp. 733-738.
Ahn et al., Plast. Reconstr. Surg. 105, 2002, pp. 778-784, abstract.
Aoki, K.R et al., *A Preclinical Comparison of the Local Muscle Weakening Efficacy, Safety, and Antigenic Potential of Botulinum Neurotoxin Serotypes A, B, and F*, Neurology 54, Apr. 2000 (Suppl 3).
Aoki, K.R. et al., *Botulinum toxin type A and other botulinum toxin serotypes: a comparative review of biochemical and pharmacological actions*; European Journal Neurology; 2001; 8 (Suppl 5):pp. 21-29.
Aoki, K.R.; *Physiology and Pharmacology of Therapeutic Botulinum Neurotoxins*; In: Kreyden OP, ed. Hyperhidrosis and Botulinum Toxin in Dermatology; Current Problems in Dermatology: Basel, Karger; 2002; 30: pp. 107-116.
Arezzo et al., Pain Med. 2:239, #202, Sep. 2001, abstract.
Ashby, P. et al., *Immediate Motor Effects of Stimulation through Electrodes Implanted in the Human Globus Pallidus*, Stereostatic and Functional Neurosurgery 70, 1998, pp. 1-18.
Ashby, P. et al., *Motor effects of stimulating the human cerebellar thalamus*, Journal of Physiology 489.1, 1995, pp. 287-298.
Awad et al., J. Child. Neurol. 1999, 14, pp. 316-319.
Barnes, Deborah M., *Debate About Epilepsy: What Initiates Seizures?* Science 86, Nov. 21, 1986, vol. 234, pp. 938-941.
Bejjani, Boulos-Paul, et al., *Bilateral subthalmic stimulation for Parkinson's Disease by Using Three-Dimensional Stereostatic Magnetic Resonance Imaging and Electrophysiological Guidance*, J. Neurosurg. 92, 2000, pp. 615-625.
Bellezza, David M., et al., *Stereotactic Interstitial Brachytherapy*, Textbook of Stereotactic and Functional Neurosurgery, Edited by Gildenberg et al., McGraw-Hill Publ., Chapter 66, pp. 577-580.
Benabid, Alim L., et al,. *Deep brain stimulation of the corpus luysi (subthalamic nucleus) and other targets in Parkinson's disease. Extension to new indications such as dystonia and epilepsy*, J Neurol 248, 2001, Suppl. 3, pp. 111/37-111/47.
Berardelli et al., Ital. J. Neurol. Sci. 18, 1997, pp. 261-269.
Berman, Robert M., et al., *A Randomized Clinical Trial of Repetitive Transcranial Magnetic Stimulation in the Treatment of Major Depression*, Biological Psychiatry 47, 2000, pp. 332-337.
Berquist, Filip et al., *Evidence for different exocytosis pathways in dendritic and terminal dopamine release in vivo*, Brain Research 950, 2002, pp. 245-253.
Billet, Sara, et al., *Cholinergic Projections to the Visual Thalamus and Superior Collicullus*, Brain Research 847, 1999, pp. 121-123.
Boltzmann, Ludwig, *Post mortem studies in Parkinson's disease—is it possible to detect brain areas for specific syndromes?* J. Neural Transm, 1999, Suppl 56, pp. 1-29.
Brem, Henry, et al., *The safety of interstitial chemotherapy with BCNU-loaded polymer followed by radiation therapy in the treatment of newly diagnosed malignant gliomas, phase 1 trial*, Journal of Neuro-Oncology 26, 1995, pp. 111-123.
Brin, Mitchell F. et al., *Botulinum Toxin Type A: Pharmacology*; In: Mayer Nathaniel H, ed. Spasticity: Etiology, Evaluation, Management and the Role of Botulinum Toxin; 2002; pp. 110-124.
Brophy, B.P., et al., *Thalamotomy for Parkinsonian Tremor*, Stereotact Funct Neurosurg 69, 1997, pp. 1-4.
Callaway et al., Sem. Cutan. Med. Surg. 20, Jun. 2001, pp. 127-136.
Canafoglia, Laura, et al., *Rhythmic Cortical Myoclonus in a Case of HIV-Related Encephalopathy*, Mov Disord, vol. 18, No. 12, 2003.
Chappell, Phillip et al., *Future Therapies of Tourette Syndrome*; Neurol Clin; 1997; vol. 15, No. 2, May; pp. 429-450.
Cmelak, Anthony J. et al.; *Low-dose stereotactic radiosurgery is inadequate for medically intractable mesial temporal lobe epilepsy: a case report*; *Seizure*; 2001, 10, pp. 442-446.

(56) References Cited

OTHER PUBLICATIONS

Czaplinski, A., et al., *Tic Syndrome*, (article in Polish), Neurol. Neurochir. Pol. Nov.-Dec. 2002, 36(6), pp. 1251-1253.

Dabrowski et al., Dev. Med. Child Neurol 47, 2005, pp. 636-639.

Danober, Neuroscience 69, 1995, pp. 1183-1193.

Davis, Karen D., et al., *Globus pallidus stimulation activates the cortical motor system during alleviation of Parkinsonian symptoms*, Nature Medicine, vol. 3, No. 6, Jun. 1977, pp. 671-674.

"Deep temporal nerves" Wikipedia page, http://en.wikipedia.org/wiki/Deep_temporal_nerves, retrieved Mar. 23, 2013.

*Diagnostic and Statistical Manual of Mental Disorders* 4th Ed.; Published by the American Psychiatric Association Washington, D.C.; pp. 108-116.

Dichter, Marc A.; Basic Mechanisms of Epilepsy: 9, 1997, pp. S2-S6 Targets for Therapeutic Intervention; *Epilepsia*; vol. 38, Suppl. 9, 1997, pp. S2-S6.

Dykstra, Dennis D. et al.; Treatment of Detrusor-Sphincter Dyssynergia with Botulinum A Toxin: A Double-Blind Study; *Arch Phys Med Rehabil*; Jan. 1990, 71, pp. 24-26.

Ferrari, David M. et al., *The protein disulphide-isomerase family: unravelling a string of folds*; Biochem J; 1999 (339) pp. 1-10.

Frankel et al., Neurology 36, 1986, pp. 378-382.

Fried, Itzhak et al.; Cerebral microdialysis combined with single-neuron and electroencephalographic recording in neurosurgical patients; *J Neurosurg*; 91, 1999, pp. 697-705.

Galarreta, Mario et al.; Frequency-dependent synaptic depression and the balance of excitation and inhibition in the neocortex; *Nature Neuroscience*; vol. 1 No. 7, Nov. 1998, pp. 587-594.

Gale, Karen; Focal trigger zones and pathways of propagation in seizure generation; *Epilepsy: models, mechanism and concepts*; Schwartzkroin, P.A. Editor, Cambridge U. Press, U.K. 1993, pp. 48-93.

Ganguly, Karunesh et al.; Enhancement of presynaptic neuronal excitability by correlated presynaptic and postsynaptic spiking; *Nature Neuroscience*; vol. 3 No. 10, Oct. 2000, pp. 1018-1026.

Gary, Mary G., et al., *Evaluation of the Efficacy of a Bioerodible Bupivacaine Polymer System on Antinociception and Inflammatory Mediator Release*, Pain 82, 1999, pp. 49-55.

Gaspar, Laurie E., et al., *Permanent[125] Iodine Implants for Recurrent Malignant Gliomas*, Int. J. Radiation Oncology Biol. Phys. vol. 43, No. 5, 1999, pp. 977-982.

George et al., Ann. Otol. Rhinol. Laryngol. 101, 1992, pp. 888-892, abstract.

Ghika, J., et al., *Bilateral contemporaneous posteroventral pallidotomy for the treatment of Parkinson's disease: neuropsychological and neurological and neurological side effects, Report of four cases and review of the literature*, J. Neurosurg, Aug. 91(2), 1999, pp. 313-321.

Giladi N., J. Neurol. Sci. 152, 1997, pp. 132-135, abstract.

Gilio, F., M.D., et al., *Effects of Botulinum Toxin Type A on Intracortical Inhibition in Patients with Dystonia*, Annals of Neurology, vol. 48, No. 1, Jul. 2000, pp. 20-26.

Granana et al., Seminars in Pediatric Neurology 6, Sep. 1999, pp. 221-224.

Greenberg et al., Neurology 54, 2000, pp. 142-147.

Gross, Jeffrey D., et al., *Pallidotomy for Parkinson's Disease*, Textbook of Stereostatic and Functional Neurosurgery, 1998, Chapter 121, pp. 1153-1160.

Gross, Robert E. et al., *Relationship of lesion location to clinical outcome following microelectrode-guided pallidotomy for Parkinson's disease*, Brain 122, 1999, pp. 405-416.

Gross, Robert E., et al., *The effects of pallidotomy on Parkinson's Disease: study design and assessment techniques*, Acta Neurochir Suppl 68, 1997, pp. 24-28.

Guyton, Arthur C. et al., Textbook of Medical Physiology 10th ed; W.B. Saunders Company; pp. 685-697.

Guyuron et al. Surgical treatment of migraine headaches. Plast Reconstr Surg. Jun. 2002; 109(7):2183-9.

Habermann, E., *Tetanus toxin and botulinum A neurotoxin inhibit and at higher concentrations enhance noradrenaline outflow from particulate brain cortex in batch*, Naunyn Schmiedebergs Arch Pharmacol 318, 1981, pp. 105-111.

Hagenah, R., et al., *Effects of Type A Botulinum Toxin on the Cholinergic Transmission at Spinal Renshaw Cells and on the Inhibitory Action at Ia Inhibitory Interneurones*, Naunyn-Schmiedeberg's Arch. Pharmacol. 299, 1977, pp. 267-272.

Heikkinen, E.R. et al.; Stereotactic Radiotherapy Instead of Conventional Epilepsy Surgery; *Acta Neurochirurgica*; 1992, 1994, pp. 159-160.

Herrera, D.G., et al., Neuroscience 35(2), 1990pp. 273-281.

Hoffmann, Ralph E., et al., *Transcranial Magnetic Stimulation and Auditory Hallucinations in Schizophrenia*, The Lancet, vol. 355, Mar. 25, 2000, pp. 1073-1075.

Hutchison, W.D. et al., *Differential neuronal activity in segments of globus pallidus in Parkinson's disease patients*, NeuroReport, vol. 5, No. 12, Jul. 21, 1994, pp. 1533-1537.

Hutchison, W.D. et al., *Effects of apomorphine on globus pallidus neurons in Parkinsonian patients*, Annals of Neurology, No. 42, No. 5, No. 1997, pp. 767-775.

Hutchison, W.D., et al,. *Identification and characterization of neurons with tremor-frequency activity in human globus pallidus*, Exp Brain Res 113, 1997, pp. 557-563.

Huttner, W.B. et al.; Exocytotic and endocytotic membrane traffic in neurons; *Current Opinion in Neurobiology*; 1991, 1, pp. 388-392.

Jackowski, Andre, *Neural injury repair: hope for the future as barriers to effective CNS regeneration become clearer*, British Journal of Neurosurgery 9, 1995, pp. 303-317.

Jankovic J., In: Therapy with Botulinum Toxin (Ed) Jankovic J., Chapter 39, 1994, pp. 503-509.

Jankovic, Joseph;*Botulinum Toxin in the Treatment of Dystonic Tics*; Movment Disorders; vol. 9, No. 3, 1994; pp. 347-349.

Jankovic, Joseph; *Botulinum Toxin in the Treatment of Tics Associated with Tourette's Syndrome*; Neurology; Apr. 1993; 43(4 Suppl 2); A310; Abstract.

Jefferys, J.G.R. et al., Chronic focal epilepsy induced by intracerebral tetanus toxin; *The Italian Journal of Neurological Sciences*; 16, 1995, pp. 27-32.

Jellinger, K.A.; Post mortem studies in Parkinson's disease—is it possible to detect brain areas for specific symptoms?; *J Neural Transm*; 1999, Suppl 56, pp. 1-29.

Jimenez-Jimenez, F.J., et al., *Pharmacological Options for the Treatment of Tourette's Disorder*, Drugs, 2001, 61(15), pp. 2207-2220.

Jitpimolmard et al., J. Neruol Neurosurg Psychiatry 64, 1998, pp. 751-757.

Kaplitt, Michael G., MD., et al., *Surgical Drug Delivery for Neurodegenerative Diseases*, Clinical Neurosurgery, 2000, vol. 48, Chapter 10, pp. 127-144.

King, David B., *Parkinson's disease levodopa complications*, The Canadian Journal of Neurological Sciences 26, 1999, Suppl 2, pp. S13-S20.

Kohl, A. et al.; Comparison of the effect of botulinum toxin A (Botox®) with the highly-purified neurotoxin (NT 201) in the extensor digitorum brevis muscle test; *Movement Disorders*; 2000, 15, Suppl 3, 165, pp. 805.

Koller, W.C. et al.; Surgical treatment of Parkinson's disease; *Journal of the Neurological Sciences*; 167, 1999, pp. 1-10.

Korolkiewicz, Pharmacological Research 37, 1998, pp. 477-483.

Kossoff, E.H., et al. *Tourette Syndrome: Clinical Characteristics and Current Management Strategies*, Paediatr Drugs 3(5), 2001, pp. 355-363.

Krack, P., et al., *Modification of a Facial Tick with Botulinum Toxin*, Mov Disord 1995, May, 10(3), p. 401.

Krauss, Joachim K. et al., Severe Motor Tics Causing Cervical Myelopathy in Tourette's Syndrome; *Movement Disorders*; vol. 11, No. 5, 1996; pp. 563-565.

Kudelko, K.M. et al., *Successful treatment of recalcitrant restless legs syndrome with botulinum toxin A*; Movment Disorders; 2002; 17 (Suppl 5); S242 ABS p. 779.

Kwak et al., Arch. Neurol. 57, 2000, pp. 1190-1193.

Kwak, C., et al., *Premonitory Sensor Phenomenon in Tourette's Syndrome*, Mov. Disord. Dec. 2003, 18(12), pp. 1530-1533.

Kwak, Carolyn, et al., *Tics in Tourette Syndrome and Botulinum Toxin*, Journal of Child Neurology, vol. 15, No. 9, Sep. 2000.

(56) References Cited

OTHER PUBLICATIONS

Kwan, P. et al.; Refractory epilepsy: a progressive, 77-84 intractable but preventable condition?; *Seizure*; 2000, 11, pp. 77-84.
Lan, J. et al.; Activation of Metabotropic Glutamate Receptor 1 Accelerates NMDA Receptor Trafficking; *The Journal of Neuroscience*; Aug. 15, 2011, 21, (16), pp. 6058-6068.
Landi, A. et al.; Accuracy of Stereotactic Localisation with Magnetic Resonance Compared to CT Scan: Experimental Findings; *Acta Neurochir*; 2001, 143, pp. 593-601.
Lang et al., Adv. Neurol. 58, 1992, pp. 25-32.
Lang et al., Ann. Neurol. 33, 1993, pp. 212-215.
Lang, A., Neurology 41, 1991, pp. 223-228.
Lang, A.E., *Update on the Treatment of Tics*, Adv. Neurol. 85, 2001, pp. 355-362.
Lavenstein, B.L., *Treatment Approaches for Children with Tourette Syndrome*, Curr Neurol Neurosci Rep, Mar. 2003, 3(2), pp. 143-148.
Leckman et al., Am. J. Psychiatry 150, 1993, pp. 98-102.
Leckman et al., Am. J. Psychiatry 151, 1994, pp. 675-680.
Lee et al., J. Clin. Psychol. 32, 1976, pp. 843-844, abstract.
Levy, Ron et al.; Lidocaine and muscimol microinjections in subthalamic nucleus reverse parkinsonian symptoms; *Brain*; 2001, 124, pp. 2105-2118.
Lomber, Stephen G.; The advantages and limitations of permanent or reversible deactivation techniques in the assessment of nueral function; *Journal of Neuroscience Methods*; 86, 1999, pp. 109-117.
Lozano, Andres et al.; Methods for microelectrode-guided posteroventral pallidotomy; *J Neurosurg*; vol. 84, Feb. 1996, pp. 194-202.
Malpeli, Joseph; Reversible inactivation of subcortical sites by drug injection; *Journal of Neuroscience Methods*; 86, 1999, pp. 119-128.
Marjama-Lyons, Jill et al., *Tremor-Predominant Parkinson's Disease*; Drugs & Aging; Apr. 16, 2000; (4) pp. 273-278.
Marras et al., Neurology 56, Mar. 2001, pp. 605-610.
Martin, J.H. et al.; Pharmacological inactivation in the analysis of the central control of movement; *Journal of Neuroscience Methods*; 86, 1999, pp. 145-159.
Matarasso, S.L., Dermatol. Surg. 29, 2003, pp. 7-13, abstract.
McCormick, David et al.; On the Cellular and Network Bases of Epileptic Seizures; *Annual Rev Physiol*; 2001, 63, pp. 815-846.
Mellanby, Jane; Tetanus Toxin as a Tool for Investigating the Consequences of Excessive Neuronal Excitation; *Botulinum and Tetanus Neurotoxins*; edited by B.R. DasGupta, Plenum Press, 1993, pp. 291-297.
Merck Manual of Diagnosis and Therapy, 2002, Rahway, N.J., pp. 378, 1436, 1491-1495, 1500.
Merck Manual, Second Home Edition, Chapter 85, online version accessed Aug. 10, 2005.
Morrell, Frank et al.; Multiple subpial transaction: a new approach to the surgical treatment of focal epilepsy; *J Neurosurg*; 70, 1989, pp. 231-239.
"Motor and Sensory nerves" For Dummies page, http://www.dummies.com/how-to/content/motor0and-sensory-facial-nerves.html, retrieved Mar. 23, 2013.
Mulligan, Lisa et al.; Multiple Subpial Transections: The Yale Experience; *Epilepsia*; 42(2), 2001, pp. 226-229.
Nadeau, Stephen E.; Parkinson's Disease; *J by the American Geriatrics Society*; 1997, 45, pp. 233-240.
Never et al., Eur. J. Neurol. 7, Jan. 2000, pp. 55-62.
Nowinski, Wieslaw et al.; Computer-Aided Stereotactic Functional Neurosurgery Enhanced by the Use of the Multiple Brain Atlas Database; *IEEE Transactions on Medical Imaging*; VI 19, No. 1, Jan. 2000, pp. 62-69.
Oakman, S.A. et al.; Characterization of the Extent of Pontomesencephalic Cholinergic Neurons' Projections to the Thalamus: Comparison with Projections to Midbrain Dopaminergic Groups; *Neuroscience*, vol. 94, No. 2, 1999, pp. 529-547.
Owe-Larsson, Bjorn et al.; Distinct Effects of Clostridial Toxins on Activity-dependent Modulation of Autaptic Responses in Cultured Hippocampal Neurons; *European Journal of Neuroscience*, vol. 9, 1997, pp. 1773-1777.

Parrent Andrew G. et al.; Stereotactic Surgery for Temporal Lobe Epilepsy; *The Canadian Journal of Neurological Sciences*, Suppl 1, S79-S96.
Parrent, Andrew G.; Stereotactic radiofrequency ablation for the treatment of gelastic seizures associated with hypothalamic hamartoma; *J Neurosurg*, 91, 1999, pp. 881-884.
Parton, R.G. et al.; Cell Biology of Neuronal Endocytosis; *Journal of Neuroscience Research*, 1993, 36, pp. 1-9.
Pauls et al., Arch. Gen. Psychiatry 43, 1986, pp. 1180-1182.
Penn, Richard D.; The Future of CNS Infusion Systems; *Textbook of Stereotactic and Functional Neurosurgery*; edited by Gildenberg et al., McGraw-Hill publishers, Chp 218, pp. 2073-2076, 1997.
Perry, Elaine et al.; Acetylcholine in mind: a neurotransmitter correlate of consciousness?; *TINS*, 1999, vol. 22, No. 6, pp. 273-280.
Physician's Desk Reference, electronic version, entry for botulinum toxin Botox accessed Feb. 25, 2005.
Playfer, J.R.; Parkinson's disease; *Postgrad Med J*; 1997, 73, pp. 257-264.
Poungvarin et al., J. Med. Assoc. 78, Thailand, 1995, pp. 281-288.
Prince, David A.; Cellular Mechanisms of Interictal-ictal Transitions; *Mechanisms of Epileptogenesis The Transition to Seizure*; edited by Dichter, published by Plenum Press, Chp 4, pp. 57-71, 1988.
Prince, David A.; Epileptogenic Neurons and Circuits; *Jasper's Basic Mechanisms of the Epilepsies Third Edition: Advances in Neurology*; vol. 79, edited by Delgado-Escuets et al., 1999, Chp 45, pp. 665-684.
Rabasseda, Toxicon 26, 1998, pp. 329-336.
Racine, Ronald J.; Modification of Seizure Activity by Electrical Stimulation: I. After-Discharge Threshold; *Electroenceph clin Neurophysiol*; 1972, 32, pp. 269-279.
Racine, Ronald J.; Modification of Seizure Activity by Electrical Stimulation: II. Motor Seizure; *Electroenceph clin Neurophysiol*; 1972, 32, pp. 281-294
Raggenbass, Mario et al.; Nicotinic Receptors in Circuit Excitability and Epilepsy; *J Neurobiol*; Dec. 2002, 53(4).
Rand, Robert W. et al.; Intratumoral Administration of Recombinant Circularly Permuted interleukin-4-Pseudomonas, Exotoxin in Patients with High-Grade Glioma; *Clinical Cancer Research*; 6(6), 2157, pp. 1-16 Abstract, 2000.
*Report of the Therapeutics and Technology Assessment Subcommittee of the American Academy of Neurology*, Neurology 40, 1990, pp. 1332-1336.
Rico, Beatriz et al.; A population of cholinergic neurons is present in the macaque monkey thalamus; *European Journal of Neuroscience*, vol. 10, 1998, 2346-2352.
Robertson, J. Child Psychol. Psychiatr. 35, 1994, pp. 597-611.
Rodriguez-Nunez, Antonio, *Syncope and Seizures: It Is Time for Evidence*, Journal of Child Neurology, vol. 15, No. 9, Sep. 2000.
Rogawski, Michael et al.; Antiepileptic Drugs: Pharmacological Mechanisms and Clinical Efficacy with Consideration of Promising Developmental Stage Compounds; *Pharmacological Reviews*; vol. 42, No. 3, pp. 223-286, 1990.
Salloway, Stephen, et al., *Botulinum Toxin for Refractory Vocal Tics*, Mov Disord 1996, 11(6), pp. 745-748.
Schafer, M.K. et al.; Cholinergic Neurons and Terminal Fields Revealed by Immunohistochemistry for the Vesicular Acetycholine Transporter. I. Central Nervous System; *Neuroscience*; vol. 84, No. 2, 1998, pp. 331-359.
Schantz, Edward J. et al., *Preparation and Characterization of Botulinum Toxin Type A for Human Treatment*; Terapy with Botulinum Toxin, edited by Jankovic et al., published by Marcel Dekker, Inc., Chpt. 3, pp. 41-49.
Schapiro, Pediatr. Nursing 28, May-Jun. 2002, pp. 243-253.
Scharfen, Cindy et al.; High *Activity Iodine-125 Interstitial Implant for Gliomas*; Int J Radiation Oncology Biol Phys; vol. 24, pp. 583-591, 1992.
Schuurman, P. R. et al.; A Comparison of Continuous Thalamic Stimulation and Thalamotomy for Suppression of Severe Tremor; *The New England Journal of Medicine*; Feb. 17, 2000, vol. 342, No. 7, pp. 461-468.
Scott, B.L., et al., *Botulinum toxin injection into vocal cord in the treatment of malignant coprolalia associated with Tourette's Syndrome*, Move. Disord., Jul. 11, 1996 (4), pp. 431-433.

(56) References Cited

OTHER PUBLICATIONS

Scremin et al., Brain Research Bulletin 45, 1998, pp. 167-174.
Sheftell et al. Migraine and psychiatric comorbidity: from theory and hypotheses to clinical application. Headache, Oct. 2002;42(9): 934-44.
Silberstein, Stephen, et al,. *Botulinum Toxin Type A as a Migraine Preventive Treatment*, Headache, Jun. 2000, 40(6), pp. 445-450.
Singer, H.S., et al,. *New Treatments for Tourette's Syndrome*, Inpharma 21, Spring 2001, No. 1284.
Smith, Epilepsia 34, 1993, pp. 43-53.
Speelman, J.D. et al.; Thalamic Surgery and Tremor; *Movement Disorders*; vol. 13, Suppl 3, 1998, pp. 103-106.
Stein et al., J. Clin. Psychiatr. 58, Apr. 1997, pp. 177-178.
Koliatsos et al., Eds. Steriade, M. et al., *Brain Cholinergic Systems*; Oxford University Press, 1990, pp. 136.
Steriade, M. et al.; Parallel activation of thalamic and cortical neurons by brainstem and basal forebrain cholinergic systems; *Brain Cholinergic Systems*; Oxford University Press, 1990, Chp 1, pp. 4-64.
Stone, Trevor W., editor, *CNS Neurotransmitters and Neuromodulators Acetylcholine*; CRC Press, 1995, pp. 16.
Sugahara, H. et al., *Psychogenic Torticollis*, Ryoikibetsu Khokogun Shirizu 38 (article in Japanese), 2003, pp. 582-586, Abstract.
Sun, Bomin et al.; Reduction of Hippocampal-Kindled Seizure Activity in Rats by Stereotactic Radiosurgery; *Experimental Neurology*; 154, 1998, pp. 691-695.
Sutula, Thomas P.; Sprouting as an underlying cause of hyperexcitability in experimental models and in the human epileptic temporal lobe; *Epilepsy: Models, Mechanisms, and Concepts*; edited by Schwartzkroin, Cambridge Univ Press, Chp 9, pp. 304-322, 1993.
Talairach, Jean et al.; editors, *Co-Planar Stereotaxic Atlas of the Human Brain*; Chapter 1: Direct and Indirect.Radiologic Localization pp. 1-4 and Chapter 2: Reference System: Basal Brain Line CA-CP pp. 5-8, 1988, Thieme Medical Publishers, Inc., N.Y.
Tarsy, D.; Botulinum Toxin Treatment is not Effective for Epilepsy Partialis Continua; *Movement Disorders*; 1995, 10(3) pp. 357-358
Tasker, Ronald R. et al.; Surgical Treatment Neurosurgery; *Textbook of Stereotactic and Functional Neurosurgery*; edited by Gildenberg et al.; Chp 105, pp. 1015-1032.
Cullen et al., Eds. Tracey, David J. et al., *Neurotransmitters in the Human Brain*; Plenum Press, 1995, pp. 136-139.
Trimble, Michael R., et al., *Vocal Tics in Gilles de la Tourette Syndrome Treated with Botulinum Toxin Injections*, Mov Disord., May 1998, 13(3), pp. 617-619.
Trudeau, Louis-Eric et al.; Modulation of an early step in the secretory machinery in hippocampal nerve terminals; *Neurobiology*; vol. 95, Issue 12, Jun. 9, 1998, pp. 7163-7168, Abstract.
Wang, Lu-Yang et al.; High-frequency firing helps replenish the readily releasable pool of synaptic vesicles; Nature; vol. 394, Jul. 23, 1998, pp. 384-388.
Weinlander et al., J. Clin. Psychol. 34, 1978, pp. 31-32.
Weinlander et al., J. Psychol. 92, 1976, pp. 77-78, abstract.
Wiebe, Samuel et al.; A Randomized, controlled Trial of Surgery for Temporal-Lobe Epilepsy; The New England Journal of Medicine; vol. 345, No. 5, Aug. 2, 2001, pp. 311-318.
Wohlfarth et al., Naunyn Schmideberg's Arch. Pharmacolo. 335, 1997, pp. 335-340.
Zigmond, et al., *Fundamental Neuroscience*; 1999 by Academic Press, San Diego, CA; pp. 963-964.

\* cited by examiner

BOTULINUM TOXIN TREATMENT OF ANXIETY AND BIPOLAR DISORDERS

CROSS REFERENCE TO RELATED APPLICATIONS

This application is a continuation of U.S. patent application Ser. No. 13/053,583, filed on Mar. 22, 2011, now U.S. Pat. No. 8,617,572; which is a continuation in part of U.S. patent application Ser. No. 10/964,898, filed Oct. 12, 2004, now U.S. Pat. No. 8,734,810; which claims the benefit of provisional application Ser. No. 60/515,362, filed Oct. 29, 2003, provisional application Ser. No. 60/556,150, filed Mar. 24, 2004 and provisional application Ser. No. 60/574,957, filed May 26, 2004, all incorporated entirely by reference.

BACKGROUND

A neurological disorder is a central nervous system malfunction. The central nervous system includes the brain. The brain includes the dorsal end of the spinal cord, medulla, brain stem, pons, cerebellum, cerebrum and cortex.

Commercially available botulinum toxin containing pharmaceutical composition are sold in the United States as BOTOX® (available from Allergan, Inc., of Irvine, Calif.), DYSPORT® (Medicis Pharmaceutical Corporation; Scottsdale, Ariz.), XEOMIN® (Merz Pharmaceuticals, Greensboro, N.C.) and MYOBLOC® (Solstice Neurosciences; Malvern, Pa.). BOTOX®, DYSPORT® and XEOMIN® are type A, and MYOBLOC® is type B.

It has been reported that use of a botulinum toxin to treat various spasmodic muscle conditions can result in reduced depression and anxiety, as the muscle spasm is reduced. Murry T., et al., *Spasmodic dysphonia; emotional status and botulinum toxin treatment*, Arch Otolaryngol 1994 March; 120(3): 310-316; Jahanshahi M., et al., *Psychological functioning before and after treatment of torticollis with botulinum toxin*, J Neurol Neurosurg Psychiatry 1992; 55(3): 229-231. It has also been proposed in U.S. Pat. No. 7,758,872 to Eric Finiz, to treat depression by use of botulinum toxin to cause paralysis of facial muscles to prevent frowning.

There is a need for an improved method of treating depression.

SUMMARY

Embodiments of the invention include a method for treating depression comprising locally administering a botulinum toxin to a trigeminal nerve of a human patient with depression, wherein administration of the botulinum toxin reduces a kindling effect upon generation of depression by decreasing peripheral sensory afferent stimulation of the central nervous system, thereby decreasing the depression.

Other embodiments of the invention include a method for treating depression comprising locally administering to a human patient a botulinum toxin subdermally, non-intramuscularly in a therapeutically effective amount to a trigeminal sensory nerve or to the vicinity of a trigeminal sensory nerve of the patient with depression wherein administration of the botulinum toxin reduces a kindling effect upon generation of depression by decreasing peripheral sensory afferent stimulation of the central nervous system, thereby treating the depression by reducing the occurrence of a symptom of the depression.

BRIEF DESCRIPTION OF THE FIGURES

The following drawings are presented to illustrate aspects and features of embodiments of the present invention.

DETAILED DESCRIPTION

Figure 1:
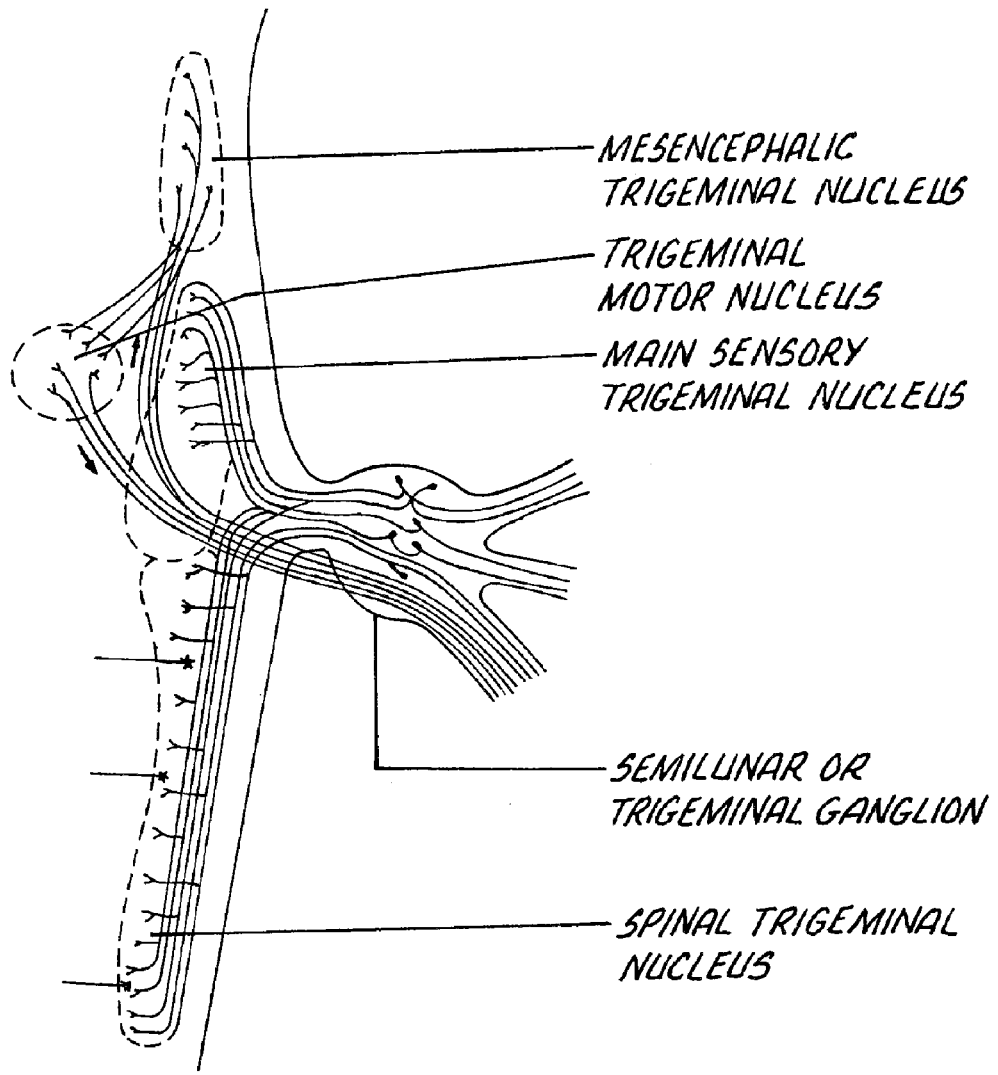
FIG. 1 is a cross sectional dorsal view of the brain stem without the cerebellum, showing locations of trigeminal nuclei.
Figure 2:
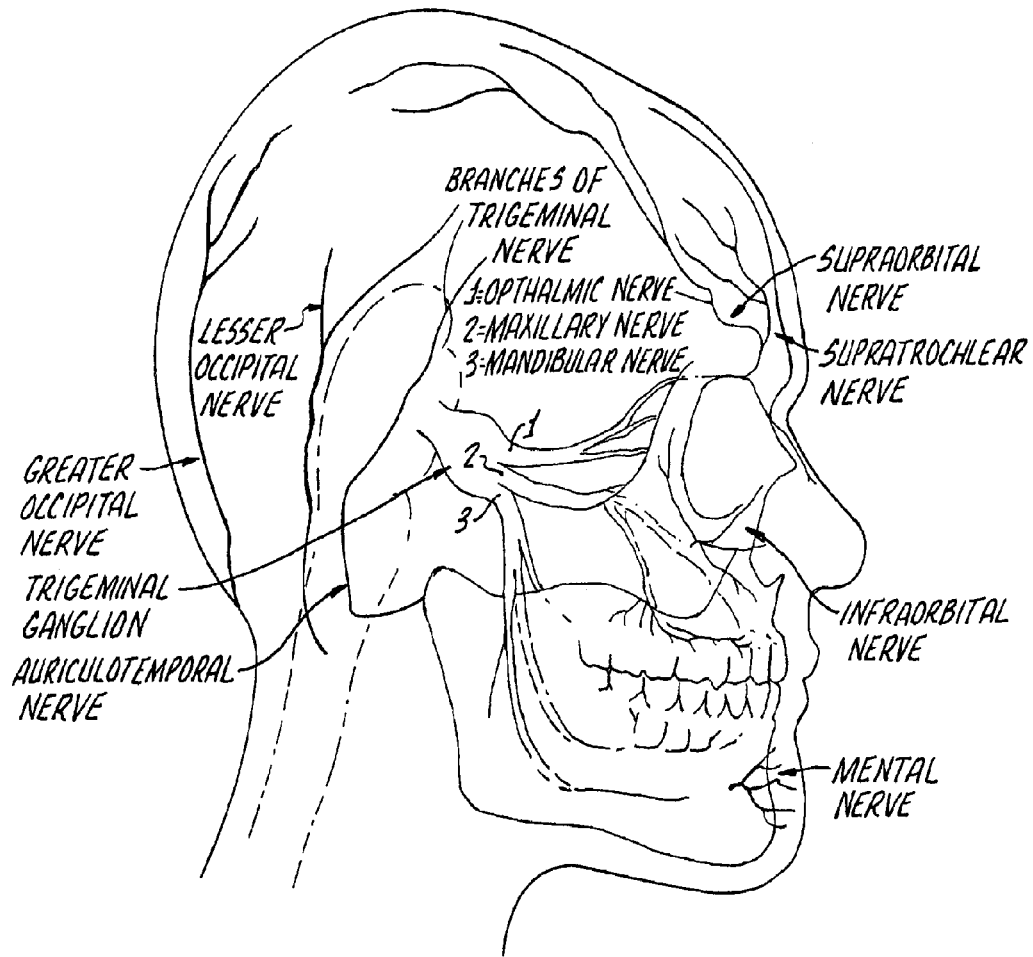
FIG. 2 is a diagrammatic representation of the locations of trigeminal nerves and spinal nerves in a human head.

The present invention is directed to medicaments and methods for treating (including alleviating and/or preventing) neuropsychiatric disorders, for example depression, in a human. In particular, the present invention is directed to a medicament containing a botulinum toxin for treating depression by administering the botulinum toxin to a trigeminal nerve.

Neuropsychiatric Disorders

A neuropsychiatric disorder is a neurological disturbance that is typically labeled according to which of the four mental faculties is affected. For example, one group of neuropsychiatric disorders includes disorders of thinking and cognition, such as schizophrenia and delirium. A second group of neuropsychiatric disorders includes disorders of mood, such as depression, affective disorders and anxiety. A third group of neuropsychiatric disorders includes disorders of social behavior, such as character defects and personality disorders. And a fourth group of neuropsychiatric disorders includes disorders of learning, memory, and intelligence, such as mental retardation and dementia. Accordingly, neuropsychiatric disorders encompass schizophrenia, delirium, Alzheimer's disease, depression, mania, attention deficit disorders, drug addiction, dementia, agitation, apathy, anxiety, psychoses, personality disorders, bipolar disorders, obsessive-compulsive disorders, eating disorders, post-traumatic stress disorders, irritability, and disinhibition.

Depression

Major depressive disorder (MDD) (also known as recurrent depressive disorder, clinical depression, major depression, unipolar depression, unipolar disorder, or simply "depression") is a mental disorder characterized by an all-encompassing low mood accompanied by low self-esteem, and by loss of interest or pleasure in normally enjoyable activities. This cluster of symptoms (syndrome) was named, described and classified as one of the mood disorders in the 1980 edition of the American Psychiatric Association's diagnostic manual. The term "depression" is ambiguous. It is often used to denote this syndrome but may refer to any or all of the mood disorders. Major depressive disorder is a disabling condition which adversely affects a person's family, work or school life, sleeping and eating habits, and general health. In the United States, around 3.4% of people with major depression commit suicide, and up to 60% of people who commit suicide had depression or another mood disorder.

The diagnosis of MDD is based on the patient's self-reported experiences, behavior reported by relatives or friends, and a mental status examination. Currently, there is no laboratory test for major depression, although physicians generally request tests for physical conditions that may cause similar symptoms. If MDD is not detected in the early stages it may result in a slow recovery and affect or worsen the person's physical health. The most common time of onset is between the ages of 20 and 30 years, with a later peak between 30 and 40 years.

Typically, patients are treated with antidepressant medication and, in many cases, also receive psychotherapy or counseling although the effectiveness of medication for mild or moderate cases is questionable. Hospitalization may be necessary in cases with associated self-neglect or a significant risk of harm to self or others. A minority are treated with electroconvulsive therapy (ECT), under a short-acting general anaesthetic. The course of the disorder varies widely, from one episode lasting weeks to a lifelong disorder with recurrent major depressive episodes. Depressed individuals have shorter life expectancies than those without depression, in part because of greater susceptibility to medical illnesses and suicide.

Schizophrenia

Schizophrenia is a disorder that affects about one percent of the world population. Three general symptoms of schizophrenia are often referred to as positive symptoms, negative symptoms, and disorganized symptoms. Positive symptoms can include delusions (abnormal beliefs), hallucinations (abnormal perceptions), and disorganized thinking. The hallucinations of schizophrenia can be auditory, visual, olfactory, or tactile. Disorganized thinking can manifest itself in schizophrenic patients by disjointed speech and the inability to maintain logical thought processes. Negative symptoms can represent the absence of normal behavior. Negative symptoms include emotional flatness or lack of expression and can be characterized by social withdrawal, reduced energy, reduced motivation, and reduced activity. Catatonia can also be associated with negative symptoms of schizophrenia. The symptoms of schizophrenia should continuously persist for a duration of about six months in order for the patient to be diagnosed as schizophrenic. Based on the types of symptoms a patient reveals, schizophrenia can be categorized into subtypes including catatonic schizophrenia, paranoid schizophrenia, and disorganized schizophrenia.

The brains of schizophrenic patients are often characterized by enlarged lateral ventricles, which can be associated with a reduction of the hippocampus and an enhancement in the size of the basal ganglia. Schizophrenic patients can also have enlarged third ventricles and widening of sulci. These anatomical characterizations point to a reduction in cortical tissue.

Although the cause of schizophrenia is not precisely known, there are several hypotheses. One hypothesis is that schizophrenia is associated with increased dopamine activity within the cortical and limbic areas of the brain. This hypothesis is supported by the therapeutic effects achieved by antipsychotic drugs that block certain dopamine receptors. In addition, amphetamine use can be associated with schizophrenia-like psychotic symptoms, and it is known that amphetamines act on dopamine receptors.

Examples of antipsychotic drugs that may be used to treat schizophrenic patients include phenothiazines, such as chlorpromazine and trifluopromazine; thioxanthenes, such as chlorprothixene; fluphenazine; butyrophenones, such as haloperidol; loxapine; mesoridazine; molindone; quetiapine; thiothixene; trifluoperazine; perphenazine; thioridazine; risperidone; dibenzodiazepines, such as clozapine; and olanzapine. Although these agents may relieve the symptoms of schizophrenia, their administration can result in undesirable side effects including Parkinson's disease-like symptoms (tremor, muscle rigidity, loss of facial expression); dystonia; restlessness; tardive dyskinesia; weight gain; skin problems; dry mouth; constipation; blurred vision; drowsiness; slurred speech and agranulocytosis.

Mania

Mania is a sustained form of euphoria that affects millions of people in the United States who suffer from depression. Manic episodes can be characterized by an elevated, expansive, or irritable mood lasting several days, and is often accompanied by other symptoms, such as, overactivity, overtalkativeness, social intrusiveness, increased energy, pressure of ideas, grandiosity, distractibility, decreased need for sleep, and recklessness. Manic patients can also experience delusions and hallucinations.

Depressive disorders can involve serotonergic and noradrenergic neuronal systems based on current therapeutic regimes that target serotonin and noradrenalin receptors. Serotonergic pathways originate from the raphe nuclei of the brain stem, and noradrenergic pathways originate from the locus ceruleus. Decreasing the electrical activity of neurons in the locus ceruleus can be associated with the effects mediated by depression medications.

Mania may results from an imbalance in certain chemical messengers within the brain. It has been proposed that mania is attributed to a decline in acetylcholine. A decline in acetylcholine may result in a relatively greater level of norepinephrine. Administering phosphotidyl choline has been reported to alleviate the symptoms of mania.

Anxiety

Anxiety disorders may affect between approximately ten to thirty percent of the population, and can be characterized by frequent occurrence of symptoms of fear including arousal, restlessness, heightened responsiveness, sweating, racing heart, increased blood pressure, dry mouth, a desire to run or escape, and avoidance behavior. Generalized anxiety persists for several months, and is associated with motor tension (trembling, twitching, muscle aches, restlessness); autonomic hyperactivity (shortness of breath, palpitations, increased heart rate, sweating, cold hands), and vigilance and scanning (feeling on edge, exaggerated startle response, difficult in concentrating). benzodiazepines, which enhance the inhibitory effects of the gamma aminobutyric acid (GABA) type A receptor, are frequently used to treat anxiety. Buspirone is another effective anxiety treatment.

Trigeminal Nerve

The trigeminal nerve has three major branches, a number of smaller branches and is the great sensory nerve of the head and neck, carrying touch, temperature, pain, and proprioception (position sense) signals from the face and scalp to the brainstem. Trigeminal sensory fibers originate in the skin, course toward the trigeminal ganglion (a sensory nerve cell body), pass through the trigeminal ganglion, and travel within the trigeminal nerve to the sensory nucleus of the trigeminal nerve located in the brainstem.

The three major branches of the trigeminal nerve are the ophthalmic ($V_1$, sensory), maxillary ($V_2$, sensory) and mandibular ($V_3$, motor and sensory) branches. The large trigeminal sensory root and smaller trigeminal motor root leave the brainstem at the midlateral surface of pons. The sensory root terminates in the largest of the cranial nerve nuclei which extends from the pons all the way down into the second cervical level of the spinal cord. The sensory root joins the trigeminal or semilunar ganglion between the layers of the dura mater in a depression on the floor of the middle crania fossa. The trigeminal motor root originates from cells located in the masticator motor nucleus of trigeminal nerve located in the midpons of the brainstem. The motor root passes through the trigeminal ganglion and combines with the corresponding sensory root to become the mandibular nerve. It is distributed to the muscles of mastication, the mylohyoid muscle and the anterior belly of the digastric. The three sensory branches of the trigeminal nerve emanate from the ganglia to form the three branches of the trigeminal nerve. The ophthalmic and maxillary branches travel in the wall of the cavernous sinus just prior to leaving the cranium. The ophthalmic branch travels through the superior orbital fissure and passes through the orbit to reach the skin of the forehead and top of the head.

The maxillary nerve enters the cranium through the foramen rotundum via the pterygopalatine fossa. Its sensory branches reach the pterygopalatine fossa via the inferior orbital fissure (face, cheek and upper teeth) and pterygopalatine canal (soft and hard palate, nasal cavity and pharynx). There are also meningeal sensory branches that enter the trigeminal ganglion within the cranium. The sensory part of the mandibular nerve is composed of branches that carry general sensory information from the mucous membranes of the mouth and cheek, anterior two-thirds of the tongue, lower teeth, skin of the lower jaw, side of the head and scalp and meninges of the anterior and middle cranial fossae.

The sensory nuclei of the trigeminal nerve are located within the brainstem, in the dorsolateral pons. The mesencephalic tract and the motor nucleus of the trigeminal nerve lie more medially. The superior cerebellar peduncle lies posteriorly. It is continuous inferiorly with the spinal nucleus of the trigeminal nerve that extends into the medulla. Superiorly, the sensory nuclei on each side are continuous with the mesencephalic nucleus.

Importantly, the sensory nuclei of the trigeminal nerve receive afferent (sensory input) fibres from: (1) the trigeminal nerve ophthalmic division (e.g. general sensation from supraorbital area, cornea, iris, ethmoid sinuses), (2) trigeminal nerve maxillary division (e.g. sensation from temple, cheek, oral cavity, upper pharynx), and (3) trigeminal nerve mandibular division (e.g. sensation from middle cranial fossa, inner cheek, anterior two thirds of the tongue, chin), (4) facial nerve (e.g. general sensation from external auditory meatus), (5) glossopharyngeal nerve (e.g. general sensation from middle ear, tonsils, oropharynx, posterior one third of the tongue), (6) vagus nerve (auricular, meningeal, internal laryngeal and recurrent laryngeal branches).

Thus, primary neurons in the trigeminal ganglion synapse on the main sensory trigeminal nucleus and on the spinal trigeminal nucleus in the brainstem. The spinal nucleus of the trigeminal system extends to the upper cervical spine, where connections with cervical dermatomes exist. These dermatomes are innervated by the cervical plexus, which has sensory branches from C1 to C4. The trigeminal nerve also innervates stretch receptors in the muscles of mastication. The cell bodies of these neurons are in the mesencephalic trigeminal nucleus in the midbrain and pons).

As indicated by FIG. 1, the ascending (afferent) second order trigeminal neurons from the main sensory trigeminal nucleus, and the ascending second order neurons from the spinal trigeminal nucleus ascend and synapse in the thalamus. Projections from the thalamus are to the facial representation of the sensory cortex. Central projections from the mesencephalic trigeminal nucleus are to the motor cortex. Thalamic projections to the sensory cortex follow a somatotopic organization. The hand and face have disproportionately greater representation on a homunculus map. This body map is not static, but dynamically controlled by the pattern of use, with increased use leading to increased cortical representation. Notably, the primary somatosensory cortex in the post central gyms, receives input from the thalamus, and projects to the secondary somatic sensory cortex in the parietal operculum. There are also efferent connections from the sensory cortex to the motor cortex. Notably, the trigeminal nerve is a very large nerve and 28% of the sensory cortex is devoted to it alone.

Botulinum Toxin

Botulinum toxin type A is the most lethal natural biological agent known to man. About 50 picograms of a commercially available botulinum toxin type A (purified neurotoxin complex, Available from Allergan, Inc., of Irvine, Calif. under the tradename BOTOX® in 100 unit vials) is a LD50 in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated LD50 of botulinum toxin type A of 0.3 ng equals 1 U is corrected for the fact that about 0.05 ng of BOTOX® equals 1 unit). One unit (U) of botulinum toxin is defined as the LD50 upon intraperitoneal injection into female Swiss Webster mice weighing 18 to 20 grams each.

Seven generally immunologically distinct botulinum toxins have been characterized, these being respectively botulinum toxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B.

The present invention is based, in part, upon the discovery that peripheral administration of a botulinum toxin can treat (including alleviate and/or prevent) a variety of neurological disorders, such as a thalamically mediated neurological disorders. Non-limiting examples of thalamically mediated disorders include epilepsy, chronic pain (such as central sensitization chronic pain, central post stroke pain, regional pain, phantom limb pain, or demyelinating disease pain), reflex sympathetic dystrophy, allodynic states; chronic neurological conditions in which kindling is part of the disease process, mood disorders (including bipolar disease) and movement disorders.

In some embodiments of the invention, a botulinum toxin can be administered to prevent development of a neurological disorder such as, for example, depression, or the like in a patient with a propensity to such a disorder. A patient with a propensity to develop depression is one who shows a genetic (e.g., family history) risk factor or behaviors which, though not truly aberrant, point to progression towards depression. In some embodiments, a botulinum toxin is administered to a patient with such propensity prior to the development of depression.

In some embodiments, a botulinum toxin can be administered to treat a patient with depression. A patient is treated when the administered botulinum toxin is effective to relieve the patient from the symptoms of depression for a duration of time. In some embodiments, a patient treated in accordance with the present invention experiences a reduction in the symptoms of depression for more than a day. In some embodiments, a patient treated in accordance with the present invention experiences a reduction in the symptoms of depression for more than a month. In some embodiments, a patient treated in accordance with the present invention experiences a reduction in the symptoms of depression for more than six months.

Without wishing to be bound by theory a physiological mechanism can be set forth to explain the efficacy of the present invention. Thus, it is known that a neurological disorder can be due to a cortical disfunction or dysregulation. A cortical dysregulation, such as an episodic paroxysmal cortical dysregulation, can be influenced by stimulation of the cortex through projections received by the cortex from the thalamus. The thalamus in turn can receive afferent fibres carrying signals (input) from peripheral sensory nerves. Thus, it can be postulated that sensory input from the periphery, to thalamus to cortex can cause or can contribute to genesis of a cortical disfunction. Hence, reduction of a peripheral sensory input to the thalamus can treat a cortical disfunction.

A kindling theory can explain episodes of cortical dysfunction (and an ensuing neurological disorder) occurring over time without or with reduced the peripheral sensory stimulus to the thalamus. Thus, a neurological disorder can be manifested as a cortical disfunction mediated or influenced by thalamic input. A thalamically mediated disorder of the cortex can result in episodic paroxysmal cortical dysregulation, as the cortex is repeatedly stimulated (indirectly) by peripheral sensory nerves that terminate in the thalamus. Over time episodes of cortical dysfunction, and the resulting thalamically mediated disorder, can occur without or with reduced the peripheral sensory stimulus. Such an occurrence of cortical dysfunction without or with a reduced sensory input can be referred to as a kindling effect. For example, it can be postulated that an episode of epilepsy or pain can be induced by repeated peripheral sensory inputs. Thus, over time, the cortex can become kindled, or sensitized, such that future episodes of epilepsy or pain can occur even without or with much less peripheral sensory input to. See Post R M et al., Shared mechanisms in affective illness, epilepsy, and migraine, *Neurology.* 1994; 44 (suppl 7: S37-S47); Goddard G V et al., A permanent change in brain function resulting from daily electrical stimulation, *Exp Neurol.* 1969; 25: 295-330; Post R M, Transduction of psychosocial stress into the neurobiology of recurrent affective disorder, *AM J Psychiatry,* 1992; 149: 999-1010; and Endicott N A, Psychophysiological correlates of "bipolarity", *J Affect Disord.* 1989; 17: 47-56.

Thus, peripheral administration of a botulinum toxin in accordance with the present invention can be carried out to decrease sensory stimulation from the periphery of the central nervous system, and thereby prevents further kindling or reduce the kindling effect upon generation of a neurological disorder, such as depression. This desired therapeutic effect of peripheral administration of a botulinum toxin is independent of muscle relaxation. In some embodiments of my invention, the administration of botulinum toxin is not into muscles. Further, the suppressive effect provided by the utilized botulinum toxin can persist for a relatively long period of time, for example, for more than two months, and potentially for several years.

In some embodiments, the botulinum toxin can be administered to and/or around the vicinity of a trigeminal nerve, such that the botulinum toxin contacts the trigeminal nerve, such as a trigeminal sensory nerve. In some embodiments, the botulinum toxin may be administered to and/or around the vicinity of a trigeminal ganglion, such that the botulinum toxin contacts the trigeminal ganglion. In some embodiments, the botulinum toxin can be administered to and/or around the vicinity of a spinal nerve such that the botulinum toxin contacts the spinal nerve, wherein the spinal nerve sends an afferent to or terminates in the thalamus. The term spinal nerve generally refers to the mixed spinal nerve, which is formed from the dorsal and ventral roots that come out of the spinal cord. The spinal nerve is the portion that passes out of the vertebrae through the intervertebral foramen. In some embodiments, the botulinum toxin may be administered to and/or around the vicinity of the trigeminal nerve, to and/or around the trigeminal ganglion, and to and/or around the vicinity of a spinal nerve, wherein the spinal nerve sends an afferent to or terminates in the thalamus.

In some embodiments, a botulinum toxin is administered to and/or around the vicinity of a trigeminal nerve, such that the botulinum toxin contacts the trigeminal nerve. As set forth above, the desired therapeutic effect of peripheral administration of a botulinum toxin can be due to a down regulation of sensory trigeminal input to the cortex. Alternately, the botulinum toxin may exert a direct central effect upon retrograde transports up the trigeminal nerve to the thalamus. For example, it has been demonstrated that peripheral, subcutaneous administration of a botulinum toxin can cause a reduction in the sensitization level of central (dorsal horn) neurons which are anatomically distant from the peripheral botulinum toxin injection site. Aoki K., et al., *Mechanisms of the antinociceptive effect of subcutaneous Botox: Inhibition of peripheral and central nociceptive processing*, Cephalalgia 2003 September; 23(7): 649 ABS P3114; Cui M., et al., *Mechanisms of the antinociceptive effect of subcutaneous Botox: Inhibition of peripheral and central nociceptive processing*, Naunyn Schmiedebergs Arch Pharmacol 2002; 365 (Suppl 2): R17.

Thus, once present in the thalamus, the botulinum toxin can decrease the ability of the thalamic neurons to stimulate the cortex, and thereby treat depression. Hence, administration of a botulinum toxin according to the present invention can be effective to reduce trigeminal sensory stimulation in the thalamus, raising a threshold level for neuronal firing at the cortical level, and thereby removing kindling input to the cortex to permit treatment of a neurological disorder, such as depression. See Bolay, H., et al., *Intrinsic brain activity triggers trigeminal meningeal afferents in a migraine model*, Nature Medicine, vol 8 (2); February 2002: 136-142 (botulinum toxin can be used to change/ameliorate the progression of chronic migraines, and there is evidence for the involvement of the trigeminal nerve in the genesis of migraine headaches); Durham P. et al., *Regulation of calcitonin gene-related peptide secretion from trigeminal nerve cells by botulinum toxin type A: implications for migraine therapy*, Headache 2004 January; 44(1): 35-43 (botulinum toxin can be used to treat migraine because of the ability of the botulinum toxin to repress calcitonin gene-related peptide release from trigeminal sensory neurons); and Aoki K., et al, *Evidence for antinociceptive activity of botulinum toxin type A in pain management*, Headache 2003 July; 43(Suppl 1): S9-S15 (There is evidence that a botulinum toxin administered to the region of a sensory nerve, such as a trigeminal nerve, can reduce central sensitization).

Embodiments of the present invention provide methods for effectively treating neuropsychiatric and/or neurological disorders, such as depression, by peripherally administering a botulinum toxin.

The following definitions apply herein.

"About" means approximately or nearly and in the context of a numerical value or range set forth herein means ±10% of the numerical value or range recited or claimed.

"Intramuscular" or "intramuscularly" means into or within (as in administration or injection of a botulinum toxin into) a striated or voluntary muscle, and excludes into or within a smooth or involuntary muscle.

"Locally administering" means directly administering a pharmaceutical at or to the vicinity of a site on or within an animal body, at which site a biological effect of the pharmaceutical is desired. Locally administering excludes systemic routes of administration, such as intravenous or oral administration.

A "neurological (or neurologic) disorder" is a central nervous system malfunction such as epilepsy, chronic pain due to central sensitization, central post stroke pain, regional pain syndrome, phantom limb pain, or depression. A neurological disorder includes a brain cortical dysfunction which is mediated by or influenced by input to the cortex from the thalamus.

Neuropsychiatric disorder" means a neurological disturbance that is typically labeled according to which of the four mental faculties are affected, and includes as well any centrally mediated disorder such as CNS generated pain (i.e. allodynia) and a movement disorder, such as epilepsy.

"Peripherally administering" or "peripheral administration" means subdermal, intradermal, transdermal, or subcutaneous administration, but excludes intramuscular administration. "Peripheral" means in a subdermal location, and excludes visceral sites.

"Trigeminal sensory nerve" means a peripheral, afferent nerve cell of the trigeminal nerve which receives or which transmits sensory signals or information from the periphery to a location within a human brain such as the brain stem, thalamus or cortex. Trigeminal sensory nerve therefore excludes trigeminal motor (efferent) nerves. Thus, trigeminal sensory nerves include the trigeminal nerve ophthalmic division, maxillary division, mandibular division, frontal branch, supra orbital nerve, supra trochlear nerve, infraorbital nerve, lacrimal nerve, nasociliary nerve, superior alveolar nerve, buccal nerve, lingual nerve, inferior alveolar nerve, mental nerve, and auriculotemporal nerve.

In accordance with embodiments of the present invention, a medicament and a method is provided for preventing or for treating a chronic neurological disorder, such as a thalamically mediated disorder, such as, for example, depression, or the like. In some embodiments, the medicament can comprise a botulinum toxin for contacting to one or more trigeminal sensory nerves of a patient, thereby preventing or treating a chronic neurological disorder, such as the thalamically mediated disorder. In some embodiments, the botulinum toxin is administered peripherally to a trigeminal sensory nerve or to a vicinity of a trigeminal nerve such that the botulinum toxin contacts the trigeminal nerve. Non-limiting examples of trigeminal sensory nerves include an ophthalmic nerve, maxillary nerve, mandibular nerve, frontal branch, supra orbital nerve, supra trochlear nerve, lacrimal nerve, nasociliary nerve, infraorbital nerve, superior alveolar nerve, buccal nerve, lingual nerve, inferior alveolar nerve, mental nerve or auriculotemporal nerve.

Further in accordance with the present invention, the method comprises contacting a trigeminal nerve and further contacting a spinal nerve that sends afferent fibres to a thalamus. In some embodiments, the botulinum toxin is administered peripherally to a sensory nerve or to a vicinity of a sensory nerve such that the botulinum toxin contacts the sensory nerve. Non-limiting examples of a spinal nerve include a lesser occipital nerve or a greater occipital nerve.

Still further in accordance with the present invention, a medicament within the scope of the present invention can be effective to prevent or treat thalamically mediated or influenced disorders such as epilepsy, chronic pain, or both. Non-limiting examples of chronic pain is central sensitization chronic pain, central post stroke pain, regional pain, phantom limb pain, or demyelinating disease pain.

In some embodiments, the botulinum toxin is administered subcutaneously, intradermally or subdermally. In some embodiments, about 1 unit to about 3000 units of a botulinum toxin are administered to each nerve. In some embodiments, about 1 unit to about 100 units of a botulinum toxin are administered to each nerve.

Methods and medicaments for treating neuropsychiatric disorders according to my invention can comprise a botulinum toxin for peripherally administering to a patient. The botulinum neurotoxin is administered in a therapeutically effective amount to alleviate at least one symptom of a neuropsychiatric disorder. The botulinum neurotoxin may alleviate symptoms associated with the neuropsychiatric disorder by reducing secretions of neurotransmitter from neurons exposed to the botulinum neurotoxin.

A suitable botulinum neurotoxin for use in a method according to my invention can be a neurotoxin made by a bacterium, for example, the neurotoxin may be made from a *Clostridium botulinum*, *Clostridium butyricum*, or *Clostridium baratii*. The botulinum toxin may be a botulinum toxin type A, type B, type C.sub.1, type D, type E, type F, or type G. The botulinum toxin can be administered in an amount of between about 10.sup.-3 U/kg and about 20 U/kg. "U/kg" is an abbreviation for units per kilogram of patient weight. The effects of the botulinum toxin can persist for between about 1 month and 5 years, and can be permanent, that is provide a cure for a neuropsychiatric disorder.

Botulinum neurotoxins suitable for use in the invention include invention include naturally produced as well recombinantly made botulinum neurotoxins, such as botulinum toxins produced by *E. coli*. In addition or alternatively, the neurotoxin can be a modified neurotoxin, that is a neurotoxin which has at least one of its amino acids deleted, modified or replaced, as compared to a native or the modified neurotoxin can be a recombinant produced neurotoxin or a derivative or fragment thereof. The neurotoxins are still able to inhibit a neurotransmitter release.

The botulinum neurotoxin is administered through a peripheral route and thereby to a site within the brain that is believed to be involved in the neuropsychiatric disorder being treated. Alternately, the botulinum neurotoxin can act to reduce peripheral sensory input to a brain location. The botulinum neurotoxin can be peripherally administered so as to reduce afferent (sensory) input to, for example, a lower brain region, the pontine region, the pedunculopontine nucleus, the locus ceruleus, or to the ventral tegmental area, for example. The botulinum neurotoxin can alleviate the symptom that is associated with or dependent upon a neurotransmitter release. The botulinum neurotoxin may also restore a balance between two neuronal systems to alleviate a neuropsychiatric disorder. The botulinum neurotoxin administered to the patient can inhibit acetylcholine release from cholinergic neurons, and can potentially inhibit dopamine release from dopaminergic neurons, and release of norepinephrine from noradrenergic neurons.

The neuropsychiatric disorders treated in accordance with the methods disclosed herein include, and are not limited to, schizophrenia, Alzheimer's disease, mania, depression, and anxiety. The botulinum neurotoxin can alleviate a positive symptom associated with the neuropsychiatric disorder, for example schizophrenia, and can begin alleviate the symptoms within a few hours to up to several (two) weeks after administration.

I have found that a botulinum toxin, such as botulinum toxin type A, can be peripherally administered in amounts between about $10^{-4}$ U/kg and about 20 U/kg to alleviate a neuropsychiatric disorder experienced by a human patient. Preferably, the botulinum toxin used is peripherally administered in an amount of between about $10^{-3}$ U/kg and about 1 U/kg. Most preferably, the botulinum toxin is administered in an amount of between about 0.1 unit and about 10 units. Significantly, the neuropsychiatric disorder alleviating effect of the present disclosed methods can persist for between about 2 months to about 6 months when administration is of aqueous solution of the neurotoxin, and for up to about five years when the neurotoxin is administered as a controlled release implant.

A particular amount of a botulinum neurotoxin administered according to a method within the scope of the disclosed invention can vary according to the particular characteristics of the neuropsychiatric disorder being treated, including its severity and other various patient variables including size, weight, age, and responsiveness to therapy. To guide the practitioner, typically, no less than about 1 unit and no more than about 50 units of a botulinum toxin type A (such as BOTOX®) is administered per injection site, per patient treatment session. For a botulinum toxin type A such as DYSPORT®, no less than about 2 units and no more about 200 units of the botulinum toxin type A are administered per administration or injection site, per patient treatment session. For a botulinum toxin type B such as MYOBLOC®, no less than about 40 units and no more about 2500 units of the botulinum toxin type B are administered per administer or injection site, per patient treatment session. Less than about 1, 2 or 40 units (of BOTOX®, DYSPORT® and MYOBLOC® respectively) can fail to achieve a desired therapeutic effect, while more than about 50, 200 or 2500 units (of BOTOX®, DYSPORT® and MYOBLOC® respectively) can result in clinically observable and undesired muscle hypotonicity, weakness and/or paralysis.

More preferably: for BOTOX®) no less than about 2 units and no more about 20 units of a botulinum toxin type A; for DYSPORT® no less than about 4 units and no more than about 100 units, and; for MYOBLOC®, no less than about 80 units and no more than about 1000 units are, respectively, administered per injection site, per patient treatment session.

Most preferably: for BOTOX® no less than about 5 units and no more about 15 units of a botulinum toxin type A; for DYSPORT® no less than about 20 units and no more than about 75 units, and; for MYOBLOC®, no less than about 200 units and no more than about 750 units are, respectively, administered per injection site, per patient treatment session. It is important to note that there can be multiple injection sites (i.e. a pattern of injections) for each patient treatment session.

Embodiments of the invention can also be used to prevent development of a neuropsychiatric disorder by administering a botulinum toxin to or to the vicinity of a trigeminal sensory nerve of the patient with a propensity to develop a neuropsychiatric disorder, thereby preventing development of the neuropsychiatric disorder. A patient with a propensity to develop a neuropsychiatric disorder is one who shows a genetic (i.e. family history) risk factor or behaviors which though not truly aberrant point to progression towards a neuropsychiatric disorder.

A botulinum toxin can be administered to and/or around one or more trigeminal nerves. These trigeminal nerves include, and are not limited to, the ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, auriculotemporal nerve and frontal branches of the trigeminal nerve. See FIG. 2. In some embodiments, botulinum toxin is administered to only one trigeminal nerve. In some embodiments, botulinum toxin is administered to more than one trigeminal nerve. In some embodiments, botulinum toxin may be administered to the trigeminal nerves simultaneously. In some embodiments, botulinum toxin may be administered to the trigeminal nerves sequentially.

In some embodiments, a botulinum toxin is administered to or around the vicinity of a spinal nerve, wherein the spinal nerve sends an afferent to or terminates in the thalamus. These spinal nerves include, and are not limited to, the lesser occipital nerve and the greater occipital nerve. See FIG. 2. In some embodiments, botulinum toxin is administered to only one spinal nerve. In some embodiments, botulinum toxin is administered to more than one spinal nerve. In some embodiments, botulinum toxin may be administered to the spinal nerves simultaneously. In some embodiments, botulinum toxin may be administered to the spinal nerves sequentially.

In some embodiments, a botulinum toxin is administered to or around the vicinity of one or more trigeminal nerve, and one or more spinal nerve, wherein the spinal nerve sends an afferent to or terminates in the thalamus. In some embodiments, botulinum toxin is administered to the ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, auriculotemporal nerve, frontal branch, lesser occipital nerve, and greater occipital nerve. In some embodiments, botulinum toxin is administered to these nerves simultaneously. In some embodiments, botulinum toxin may be administered to these nerves sequentially.

The botulinum toxin can be administered to any region of the nerves indicated herein. In some embodiments, the botulinum toxin is administered to the nerve endings. For example, the botulinum toxin may be administered subcutaneously, intradermally and/or subdermally.

The botulinum toxins used in accordance with the invention can inhibit transmission of chemical or electrical signals between select neuronal groups that are involved in generation, progression and/or maintenance of a thalamically mediated disorder. The botulinum toxins used can inhibit neurotransmission by reducing or preventing exocytosis of a neurotransmitter from particular neurons exposed to the neurotoxin. In some embodiments, the botulinum toxins can reduce neurotransmission by inhibiting the generation of action potentials of particular neurons exposed to the toxin.

Examples of suitable botulinum toxins which may be used to prevent or treat thalamically mediated disorders include botulinum toxins made from *Clostridium* bacteria, such as *Clostridium botulinum, Clostridium butyricum* and *Clostridium baratii*. The botulinum toxins may be selected from a group of botulinum toxin types A, B, C (e.g., C.sub.1), D, E, F, and G. In some embodiments, the botulinum toxin administered to the patient is botulinum toxin type A. Botulinum toxin type A is desirable due to its high potency in humans, ready availability, and known use for the treatment of muscle disorders when administered by intramuscular injection.

In some embodiments, the present invention also includes the use of (a) botulinum toxins obtained or processed by bacterial culturing, toxin extraction, concentration, preservation, freeze drying, and/or reconstitution; and/or (b) modified or recombinant botulinum toxins, that is botulinum toxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These botulinum toxin variants should retain the ability to inhibit neurotransmission between or among neurons, and some of these variants may provide increased durations of inhibitory effects as compared to native botulinum toxins, or may provide enhanced binding specificity to the neurons exposed to the botulinum toxins. These botulinum toxin variants may be selected by screening the variants using conventional assays to identify neurotoxins that have the desired physiological effects of inhibiting neurotransmission.

Botulinum toxins suitable for use in the invention include naturally produced as well recombinantly made botulinum toxins, such as botulinum toxins produced by *E. coli*. In some embodiments, the toxin may be a modified toxin, that is, a neurotoxin which has at least one of its amino acids deleted, modified or replaced, as compared to a native toxin. In some embodiments, the toxin is a chimera toxin.

In some embodiments, a composition may only comprise a single type of a botulinum toxin, such as a botulinum toxin type A, as the active ingredient to suppress neurotransmission. In some embodiments, a composition may include two or more types of botulinum toxins, which may provide enhanced therapeutic effects upon a thalamically mediated disorder. For example, a composition administered to a patient may include botulinum toxin type A and botulinum toxin type B. Administering a single composition containing two different botulinum neurotoxins may permit the effective concentration of each of the botulinum neurotoxins to be lower than if a single botulinum neurotoxin is administered to the patient while still achieving the desired therapeutic effects. The composition administered to the patient may also contain other pharmaceutically active ingredients, such as, protein receptor or ion channel modulators, in combination with the botulinum neurotoxin or botulinum neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxazepam, lorazepam, prazepam, alprazolam, halazepam, chlordiazepoxide, and clorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat neuropsychiatric disorders may include one or more botulinum toxins, in addition to ion channel receptor modulators that can reduce neurotransmission.

In some embodiments, a composition comprising a botulinum toxin is administered peripherally, and a composition containing other pharmaceutical agents, such as antipsychotics, that can cross the blood brain barrier can be administered systemically, such as by intravenous administration, to achieve the desired therapeutic effects.

In some embodiments, the botulinum toxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum toxins that may not have a functional targeting moiety (e.g., a portion of the toxin that binds to a neurotoxin receptor), and/or a translocation domain). By way of example, and not by way of limitation, a fragment of a botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its toxic effects within the cell. The pH of the target tissue is only temporarily lowered so that neuronal and/or glial injury is reduced.

Methods of administration include injecting a composition (e.g. a solution) comprising the botulinum toxin as described above. In some embodiments, the method of administration includes implanting a controlled release system that controllably releases the botulinum toxin to the target trigeminal tissue. For example, the botulinum toxin can be administered peripherally using a subdermal implant. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the botulinum toxin may be administered so that the botulinum toxin primarily effects neural systems believed to be involved in a selected thalamically mediated disorder, and does not have negatively adverse effects on other neural systems.

The present invention is also based upon the discovery that peripheral administration of a botulinum neurotoxin can provide significant and long lasting relief from a variety of different neuropsychiatric disorders.

Without wishing to be bound by theory, peripheral administration of a botulinum toxin according to the methods disclosed herein is believed to permit a botulinum neurotoxin to either be administered (by retrograde progression of the botulinum toxin) to a site within a patient's cranium and/or to reduce afferent, sensory input to a site within the patients' cranium to thereby influence intracranial neurons involved in a neuropsychiatric disorder.

Thus, neuropsychiatric disorders are believed to originate from episodic paroxysmal cortical dysregulation, influenced by various stress factors (Post R M, Silberstein S D. Shared mechanisms in affective illness, epilepsy, and migraine. *Neurology*. 1994; 44(suppl 7: S37-S47). Over time these episodes of cortical dysfunction, and the resulting neuropsychiatric disorder, can occur without stressor inputs. Hence a kindling model (Goddard G V, Mcintyre D C, Leech C K, A permanent change in brain function resulting from daily electrical stimulation *Exp Neurol*. 1969; 25: 295-330; Post R M, Transduction of psychosocial stress into the neurobiology of recurrent affective disorder. *AM J Psychiatry*, 1992; 149: 999-010) for development of a neuropsychiatric disorder is appropriate. Under a kindling model repeated low levels of stimulation can over time result in occurrence of a neuropsychiatric disorder without further sensory input. It is known that the brain can become kindled or sensitized, such that pathways inside the central nervous system are reinforced and future episodes of, for example, depression, hypomania, mania, bipolar disorder or epilepsy can then occur independently of an outside stimulus with greater and greater frequency. My kindling theory of neuropsychiatric disorders is supported by descriptions states of physiologic responsivity and heightened reactivity (Endicott NA Psychophysiological correlates of "bipolarity." *J Affect Disord.* 1989; 17: 47-56). A botulinum toxin can be used to decrease afferent stimulation of the central nervous system and thereby prevent further kindling of a neuropsychiatric disorder.

Thus, a neuropsychiatric disorder can be treated by decreasing afferent stimulation of the cortex. In particular, administration of a botulinum toxin to a site or sites around a trigeminal nerve and $c_2/c_3$ afferent the result can be a decreased responsiveness in the nucleus caudalis. This in turn can decrease thalamic and subsequent cortical afferent, sensory input. It is known that $c_2/c_3$ afferents project to the trigeminal complex and are involved with sensitization of $2^{nd}$ and $3^{rd}$ order neurons. Significantly, it has been demonstrated that peripheral, subcutaneous administration of a botulinum toxin can cause a reduction in the sensitization level of central (dorsal horn) neurons which are anatomically distant from the peripheral botulinum toxin injection site. Aoki K., et al., *Mechanisms of the antinociceptive effect of subcutaneous Botox: Inhibition of peripheral and central nociceptive processing*, Cephalalgia 2003 September; 23(7): 649 ABS P3114; Cui M., et al., *Mechanisms of the antinociceptive effect of subcutaneous Botox: Inhibition of peripheral and central nociceptive processing*, Naunyn Schmiedebergs Arch Pharmacol 2002; 365(Suppl 2): R17.

Thus, a botulinum toxin can be used to treat a neuropsychiatric disorder by blocking the progression of a neuropsychiatric disorder that can occur due to repeated sensory input to the cortex from a peripheral trigeminal sensory nerve. Notably, it has been reported that a botulinum toxin can be used to change (ameliorate) the progression of chronic migraines, and there is evidence for the involvement of the trigeminal nerve in the genesis of migraine headaches. Bolay, H., et al., *Intrinsic brain activity triggers trigeminal meningeal afferents in a migraine model*, Nature Medicine, vol 8 (2); February 2002: 136-142. Additionally, there is evidence that a botulinum toxin can be used to treat migraine because of the ability of the botulinum toxin to repress calcitonin gene-related peptide release from trigeminal sensory neurons. Durham P. et al., *Regulation of calcitonin generelated peptide secretion from trigeminal nerve cells by botulinum toxin type A: implications for migraine therapy*, Headache 2004 January; 44(1): 35-43.

Thus, peripheral administration of a botulinum toxin, by decreasing afferent trigeminal cortical stimulation, can remove external stressors which centrally kindle occurrence of a neuropsychiatric disorder. Conditions that can be treated or attenuated with this approach to reduce cortical sensory input through a trigemino-thalamic route include: central pain syndromes particularly chronic pain syndromes with central sensitization; post stroke pain syndrome; reflex sympathetic dystrophy; phantom limb pain; allodynic states; chronic neurological conditions in which kindling is part of the disease process; epilepsy; neuropsychiatric disorders, including mood disorders, particularly bipolar disease, and movement disorders.

Thus, a method according to embodiments of the invention uses a botulinum toxin to produce a modulating effect on the central nervous system when administered (i.e. injected) into a trigeminal nerve branch and/or ansa cervicalis branch particularly in the C2 and C3 dermatomes. The trigeminal sensory nerve endings that are targeted include the supra-orbital, supra-trochlear, temporo-auricular, greater and lesser occipital nerves. This method leads to decreased sensory afferents to the spinal tract of the nucleus caudalis and thereby to decreased central afferent input to the thalamus and thence to the cortex.

Hence, administration of a botulinum toxin according to embodiments of the invention is carried out so to achieve a desired central effect, that is the raising of a threshold level for neuronal firing at the cortical level, by reducing trigeminal sensory input and thereby removing kindling input to the cortex. By doing so a centrally mediated neuropsychiatric disorder can be treated. Thus, the efficacy of the present invention can be due to a reduction of a kindling effect upon the cortex, as a kindling effect reduction results in a slowing down of the progression, or the treating, of a centrally mediated neuro-psychiatric disorder.

There is evidence that a botulinum toxin administered to the region of a sensory nerve, such as a trigeminal nerve, can reduce central sensitization. Aoki K., et al, *Evidence for antinociceptive activity of botulinum toxin type A in pain management*, Headache 2003 July; 43(Suppl 1): S9-S15; Durham P., et al., *Regulation of calcitonin gene-related peptide secretion from trigeminal nerve cells by botulinum toxin type A: implications for migraine therapy*, Headache 2004 January; 44(1): 35-43.

Thus, decreasing afferent impulses in the trigeminal innervated regions can decrease central afferents initially in the brainstem and subsequently in the thalamus, the sensory cortex, and in the motor cortex. Hence, a neuropsychiatric disorder can be treated by for example, inhibiting a kindling effect, and down regulating sensory input to central afferents.

Input to the caudal segment of the spinal trigeminal nucleus from the cervical plexus branches include the greater and lesser occipital nerves, which travel over the occipital and suboccipital regions. Other nerves include the greater auricular nerve, and the anterior cutaneous nerve of the neck. In a preferred embodiment of my invention a botulinum toxin is administered delivered to these trigeminal nerve branches which run in the dermal region.

The treatment outlined above is expected to down regulate central nervous system activation and reduce kindling over the long-term. This effect is independent of muscle relaxation. Injections need to be in the region of the trigeminal and cervical plexus branches, and not in muscles of the face, neck and head.

The aim of the outlined treatment is to maximize the effects on the cortical homunculus. Using the trigeminal sensory system approach, each unit of a botulinum toxin delivered has the maximum cortical effects on the head/face representation in the homunculus, with the least side effects. This allows for the maximum central effect of each unit of botulinum toxin delivered peripherally.

An alternate theory for the efficacy (therapeutic result) of a method practiced according to the present invention rests upon the fact that a botulinum toxin, can inhibit neuronal exocytosis of several different CNS neurotransmitters, for example acetylcholine. It is known that cholinergic neurons are present throughout the brain. Additionally, cholinergic nuclei exist in the basal ganglia or in the basal forebrain, with projections to cerebral regions involved in emotion, behavior, and other cognitive functions. Thus, target tissues for a method within the scope of the present invention can include neurotoxin induced reversible denervation of brain cholinergic systems, such as basal nuclei or pedunculopontine nucleus. For example, peripheral injection or peripheral implantation of a botulinum neurotoxin to or to the vicinity of a trigeminal nerve can permit the botulinum toxin to be retrograde transported to a cholinergic brain nucleus with the result of (1) downregulation of dopaminergic release from target sites of cholinergic neurons due to the action of the toxin upon cholinergic terminals projecting into the ventral tegmental area from pedunculopontine nucleus; and (2) attenuation of ventral tegmental area output due to the action of the toxin upon cholinergic neurons projecting to the ventral tegmental area.

Alternately, use of a botulinum toxin as set forth herein can inhibit of exocytosis of nonacetylcholine neurotransmitters. For example, it is believed that once the proteolytic domain of a botulinum toxin, is incorporated into a target neuron, the toxin inhibits release of any neurotransmitter from that neuron. Thus, the botulinum neurotoxin can be peripherally administered to a target brain nuclei containing a substantial number of dopaminergic neurons so that the neurotoxin effectively inhibits the release of dopamine from those neurons. Similarly, the botulinum neurotoxin can be administered to other nuclei such as the Raphe nuclei to inhibit serotonin exocytosis, the locus ceruleus nuclei to inhibit norepinephrine exocytosis.

The botulinum neurotoxins used in accordance with the invention disclosed herein can inhibit transmission of chemical or electrical signals between select neuronal groups that are involved in generation, progression and/or maintenance of a neuropsychiatric disorder. The botulinum neurotoxins used, at the dose levels used, are not cytotoxic to the cells that are exposed to the neurotoxin. The botulinum neurotoxins used can inhibit neurotransmission by reducing or preventing exocytosis of a neurotransmitter from particular neurons exposed to the neurotoxin. Alternately, the botulinum neurotoxins can reduce neurotransmission by inhibiting the generation of action potentials of particular neurons exposed to the toxin. The neuropsychiatric disorder suppressive effect provided by the utilized botulinum neurotoxin can persist for a relatively long period of time, for example, for more than two months, and potentially for several years.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Preferably, the botulinum neurotoxin is peripherally administered by administering it to or to the vicinity of a trigeminal nerve or to a trigeminal nerve branch or trigeminal ganglion nuclei. This methods of administration permit the botulinum neurotoxin to be administered to and/or to affect select intracranial target tissues. Methods of administration include injection of a solution or composition containing the botulinum neurotoxin, as described above, and include implantation of a controlled release system that controllably releases the botulinum neurotoxin to the target trigeminal tissue. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin primarily effects neural systems believed to be involved in a selected neuropsychiatric disorder, and does not have negatively adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor), and/or a translocation domain). By way of example, and not by way of limitation, a fragment of a botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its toxic effects within the cell. The pH of the target tissue is only temporarily lowered so that neuronal and/or glial injury is reduced.

The botulinum neurotoxin is administered peripherally, and a composition containing other pharmaceutical agents, such as antipsychotics, that can cross the blood brain barrier can be administered systemically, such as by intravenous administration, to achieve the desired therapeutic effects.

Implants that are employed in accordance with the present invention may comprise various polymers. For example, a polyanhydride polymer, Gliadel® (Stolle R & D, Inc., Cincinnati, Ohio) a copolymer of poly-carboxyphenoxypropane and sebacic acid in a ratio of 20:80 has been used to make implants, and has been peripherally implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo—Controlled Trial of Safety and Efficacy of Intraoperative Controlled Delivery by Biodegradable Polymers of Chemotherapy for Recurrent Gliomas*, Lancet 345; 1008-1012: 1995.

In some embodiments, implants useful in practicing the methods disclosed herein may be prepared by mixing a desired amount of a stabilized botulinum toxin (such as non-reconstituted BOTOX® or DYSPORT) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58; 672-684: 1998.

The amount of a botulinum toxin selected for peripheral administration to a target tissue according to the present disclosed invention can be varied based upon criteria such as the thalamically mediated disorder being treated, its severity, the extent of brain tissue involvement or to be treated, solubility characteristics of the neurotoxin toxin chosen as well as the age, sex, weight and health of the patient. For example, the extent of the area of brain tissue influenced is believed to be proportional to the volume of neurotoxin injected, while the quantity of the thalamically mediated disorder suppressant effect is, for most dose ranges, believed to be proportional to the concentration of the botulinum toxin peripherally administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

As used herein, dose of a non-botulinum toxin type A is an equivalent to a dose of botulinum toxin type A if they both have about the same degree of prevention or treatment when administered to a human (although their duration may differ). The degree of prevention or treatment may be measured by the an evaluation of the improved patient function criteria set forth below.

The botulinum toxin can be peripherally administered according to the present disclosed methods in amounts of between about $10^{-4}$ U/kg to about 20 U/kg (units of type A), or an equivalent of U/kg of a non-type A botulinum toxin. A dose of about $10^{-4}$ U/kg can result in a thalamically mediated disorder suppressant effect if delivered to a small target brain nuclei. Peripheral administration of less than about $10^{-4}$ U/kg of a botulinum toxin does not result in a significant or lasting therapeutic result. A peripheral dose of more than about 20 U/kg of a botulinum toxin (such as BOTOX) poses a risk of systemic effects. Accordingly, administration of a botulinum toxin to an intracranial target tissue involved in thalamically mediated disorders through a peripheral route as set forth herein can effectively reduce symptoms associated with the thalamically mediated disorder to be treated without causing significant undesired cognitive dysfunction. Thus, the methods of the present invention can provide a more selective treatment with fewer undesirable side effects than current systemic therapeutic regimes.

In some embodiments, about 1 unit to about 40 units of botulinum toxin type A, or the equivalent of other types, are administered to a trigeminal and/or spinal nerve in accordance with the present invention. In some embodiments, about 3 units to about 30 units of botulinum toxin type A, or the equivalent of other types, are administered to a trigeminal or spinal nerve in accordance with the present invention. In some embodiments, about 5 units to about 25 units of botulinum toxin type A, or the equivalent of other types, are administered to a trigeminal or spinal nerve in accordance with the present invention. In some embodiments, about 5 units to about 15 units of botulinum toxin type A, or the equivalent of other types, are administered to a trigeminal or spinal nerve in accordance with the present invention.

In some embodiments, one or more nerve is injected with a botulinum toxin to treat a thalamically mediated disorder: supra-orbital nerve (bilaterally about 5 units of type A, or the equivalent of other types, on each side), supra-trochlear nerve (about 5 units of type A, or the equivalent of other types, on each side), frontal branches of the trigeminal nerve (about 12.5 units type A, or the equivalent of other types, each side), auriculotemporal nerve (about 20 units of type A, or the equivalent of other types, on each side), lesser occipital nerve (about 5 units of type A, or the equivalent of other types, on each side), and/or greater occipital nerve (about 5 units of type A, or the equivalent of other types, on each side). In some embodiments, the total dose administered per session is about 105 units of botulinum toxin type A, or the equivalents of other types.

In some embodiments, the particular amount of a botulinum toxin administered according to a method within the scope of the disclosed invention can vary according to the particular characteristics of the thalamically mediated disorder being treated, including its severity and other various patient variables including size, weight, age, and responsiveness to therapy. As a general guide, typically, no less than about 1 unit and no more than about 50 units of a botulinum toxin type A (such as BOTOX®) is administered per injection site, per patient treatment session. For a botulinum toxin type A such as DYSPORT®, no less than about 2 units and no more about 200 units of the botulinum toxin type A are administered per administration or injection site, per patient treatment session. For a botulinum toxin type B such as MYOBLOC®, no less than about 40 units and no more about 2500 units of the botulinum toxin type B are administered per administer or injection site, per patient treatment session. Less than about 1, 2 or 40 units (of BOTOX®, DYSPORT® and MYOBLOC® respectively) can fail to achieve a desired therapeutic effect, while more than about 50, 200 or 2500 units (of BOTOX®, DYSPORT® and MYOBLOC® respectively) can result in clinically observable and undesired muscle hypotonicity, weakness and/or paralysis.

In some embodiments, for BOTOX®), no less than about 2 units and no more about 20 units of a botulinum toxin type A; for DYSPORT® no less than about 4 units and no more than about 100 units, and; for MYOBLOC®, no less than about 80 units and no more than about 1000 units are, respectively, administered per injection site, per patient treatment session.

In some embodiments, for BOTOX no less than about 5 units and no more about 15 units of a botulinum toxin type A; for DYSPORT® no less than about 20 units and no more than about 75 units, and; for MYOBLOC®), no less than about 200 units and no more than about 750 units are, respectively, administered per injection site, per patient treatment session. It is important to note that there can be multiple injection sites (i.e. a pattern of injections) for each patient treatment session.

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

A method for treating depression according to the invention disclosed herein has many benefits and advantages, including the following:

1. the symptoms of a neurological disorder, such as a thalamically mediated disorder, can be dramatically reduced or eliminated.

2. the symptoms of a thalamically mediated disorder can be reduced or eliminated for at least about two weeks to about six months per injection of neurotoxin and for from about one year to about five years upon use of a controlled release neurotoxin implant.

3. few or no significant undesirable side effects occur from an intradermal or subdermal) injection or implantation of the botulinum toxin.

4. the present methods can result in the desirable side effects of greater patient mobility, a more positive attitude, and an improved quality of life.

EXAMPLES

The following non-limiting examples provide those of ordinary skill in the art with possible case scenarios and specific methods to treat conditions within the scope of the present invention and are not intended to limit the scope of the invention. In the following examples various modes of peripheral administration of a botulinum toxin can be carried out. For example, by topical application (cream or transdermal patch), subcutaneous injection, or subdermal implantation of a controlled release implant.

Example 1

Supraorbital and Suspratrochlear Administration of Botulinum Toxin

The supraorbital and suspratrochlear nerves innervate the frontal part of scalp and forehead. Both nerves are branches of the first division or ophthalmic branch of the trigeminal nerve. The supraorbital nerve exits the skull through the supraorbital foramen that lies in the midpupillary line, which is approximately 2.5 cm lateral to the facial midline along the supraorbital ridge. The suspratrochlear nerve exits the skull along the upper medial corner of the orbit in the suspratrochlear notch, which is approximately 1.5 cm medial to the supraorbital foramen.

Supraorbital and suspratrochlear administration of botulinum toxin may be performed from either the area of the supraorbital foramen or the area of the suspratrochlear notch. If performed from the supraorbital foramen, the area should be located, and a skin wheal raised at the site. The needle is inserted through the anesthetized area and advanced to the bone. Approximately 5 units of botulinum toxin (e.g., type A) is injected outside the foramen at the level of the inferior frontalis muscle.

The suspratrochlear nerve may be reached by advancing the needle 1.5 cm medial to the junction of the supraorbital ridge and the root of the nose. As before, about 5 units of botulinum toxin (e.g., type A) is injected.

If the injection is performed from the area of the suspratrochlear nerve, a wheal should be placed over the root of the nose at the junction of the nasal root and supraorbital ridge. The skin is infiltrated along the length of the entire eyebrow. When this injection is used, patients should be warned about the possibility of swelling in the upper and/or lower eyelids. For this type of injection, about 5 units of botulinum toxin (e.g., type A) per side is usually sufficient, and no more than 20 units should be injected into either side. As with any injection, the risk of ecchymosis or hematoma formation exists.

Example 2

Infraorbital Administration of Botulinum Toxin

The infraorbital nerve innervates the lower eyelid, medial aspect of the cheek, upper lip, and lateral portion of the nose. It is a branch of the second division or maxillary branch of the trigeminal nerve. The infraorbital nerve exits the skull through the infraorbital foramen, which is 1 cm inferior to the infraorbital ridge and approximately 2.5 cm lateral to the facial midline in the midpupillary line. After exiting the infraorbital foramen, the infraorbital nerve divides into 4 branches: the inferior palpebral, internal nasal, external nasal, and superior labial branches.

An infraorbital injection may be performed in 2 ways: via direct cutaneous injection or via intraoral injection. The infraorbital foramen should be palpated, and approximately 5 units of botulinum toxin (e.g., type A) is injected near, but not into, the canal to surround the nerve.

If the injection is to be performed via the intraoral approach, the application of a topical anesthetic to the mucosa before injection may increase patient comfort. The infraorbital foramen should be palpated with the middle finger of one hand while the thumb and index finger of the same hand are used to raise the lip. During palpation of the foramen, the needle is inserted into the superior labial sulcus at the apex of the canine fossa. Approximately 5 units of botulinum toxin (e.g., type A) is injected in the vicinity of the infraorbital foramen.

It is advisable to warn patients that swelling of the lower eyelid and ecchymosis may occur with the infraorbital injection. In addition, if anesthetic solution is injected into the orbit, excessive pain, diplopia, exophthalmos, and blindness can occur. The likelihood of the reactions is increased if the needle is placed superior to the infraorbital rim or into the infraorbital foramen.

Example 3

Mental Nerve Administration of a Botulinum Toxin

The mental nerve innervates the lower lip and chin. It is a branch of the third division or mandibular portion of the trigeminal nerve. The mental nerve exits the skull through the mental foramen, which is located approximately 2.5 cm from the midline of the face in the midpupillary line.

Either a cutaneous or intraoral approach can be used to inject the mental nerve. To inject the nerve cutaneously, the foramen should be palpated, and a wheal of botulinum toxin placed. Then, the needle should be reinserted and advanced to the vicinity of the mental foramen but not into it. Approximately 5 units of botulinum toxin (e.g., type A) should be injected into the area. Alternatively, when an intraoral approach is used, the foramen should be palpated with the middle finger of one hand and the lip lifted by the thumb and index finger of the same hand. The needle should be inserted at the inferior labial sulcus at the apex of the first bicuspid and 5 units of botulinum toxin (e.g., type A) injected.

Example 4

Use of a Botulinum Toxin to Treat a Bipolar Disorder

A female patient 24 years of age can experience rapid mood cycles from depression to euphoria which can require frequent admissions to psychiatric units and she is diagnosed with bipolar disorder. Thirty units of a botulinum toxin type can be administered subdermally around branches of the trigeminal nerve and cervical plexus. Specifically, one of more of the following locations can be administered (such as by injection) the botulinum toxin: (1) the frontal branch of the ophthalmic division-of the trigeminal nerve divides in the orbit into the suspratrochlear nerve and the supraorbital nerve. The suspratrochlear nerve exits the orbit between the trochlea and the supraorbital foramen. The supraorbital nerve exits from the superior aspect of the orbit passing through the supraorbital foramen. The supratrochlear and supraorbital nerve branches of the trigeminal nerve can be localized for administration of a botulinum toxin thereto by the supraorbital foramen or notch. Both of these nerves then travel under the frontalis muscle and above the periosteum. Thus, a botulinum toxin can be administered below the frontalis muscle and above the periosteum to infiltrate these peripheral branches (supratrochlear and supraorbital nerves) of the trigeminal nerve. (2) The auriculotemporal branch of the trigeminal nerve arises from the mandibular division of the trigeminal nerve and exits in the region of the temporomandibular joint at which location the botulinum toxin can be administered. (3) The superficial temporal branches of the trigeminal nerve accompany the superficial temporal artery which is easily palpated for administration of a botulinum toxin along its' course. (4) The cervical rami of the trigeminal give rise to the greater and lesser occipital nerves to which a botulinum toxin can be administered at the location where they cross the nuchal ridge just medial and lateral to the palpable occipital artery which lies midway between the mastoid process and the inion. (5) The rami of the lower cervical nerves of the trigeminal nerve can be infiltrate with a botulinum toxin at the location where they penetrate the semispinalis muscle and trapezius muscle. Thus, administration of the botulinum toxin can be, for example, to one or more of these five trigeminal nerve branch sites. After treatment, the patients' bipolar condition can improve within several weeks.

Example 5

Treatment of Mania with Botulinum Toxin Type A

A 44 year old male can be diagnosed with mania. Thirty units of a botulinum toxin type A can be subdermally, non-intramuscularly injected around branches of the trigeminal nerve and cervical plexus, as set forth by Example 4. The patient's manic symptoms can subside within 1-7 days, and can remain substantially alleviated for between about 2 months to about 6 months per toxin injection or for between about 1 to 5 years depending upon the particular release characteristics of an implant polymer which can be inserted and the quantity of the botulinum toxin loaded therein. Notably, there can be significant attenuation of the manic behavior and the patient has a substantially more controlled behavioral pattern.

Example 6

Treatment of Depression with Botulinum Toxin Type A

A 58 year old female with a strong family history of depression presents for assessment to her psychiatrist. She has a strong family history of depression and has had disabling depression since her teens. She has been tried on numerous oral medications without benefit. She is not suicidal. At times she is agitated and this fluctuates with lethargy and insomnia. She is referred to a neurologist to rule out any secondary causes for her symptoms. Brain MRI scan and routine lab testing is within normal limits. After a discussion with her psychiatrist about the underlying causes for refractory depression, a trial of botulinum toxin type A is recommended. Multiple injections are done to areas supplied by peripheral trigeminal sensory nerves, as described in Example 4. At each site a low dose is used and there is no cosmetic effect from this treatment. A total of 155 units is administered. Follow up visits every 4 weeks thereafter reveal improving subjective depression symptoms with less agitation, improved energy levels and sleep patterns. Beck's depression score improves from 20 at baseline to 8 at 3 months. A second treatment of botulinum toxin type A is given at 3 months. The patient continues to improve and is functioning normally at 6 months. No side effects are reported.

Example 7

Treatment of Depression with Botulinum Toxin Type B

The same patient in Example 6 above with the same injection paradigm, only treatment is with therapeutically effective amounts of Type B.

Various modifications of the invention, in addition to those described herein, will be apparent to those skilled in the art from the foregoing description. Such modifications are also intended to fall within the scope of the appended claims.

All references, articles, patents, applications and publications set forth above are incorporated herein by reference in their entireties.

What is claimed is:

1. A method for treating an anxiety disorder in a patient in need thereof, comprising directly administering a botulinum toxin to a trigeminal nerve of the patient, thereby treating the anxiety disorder.

2. The method of claim 1, wherein the botulinum toxin is botulinum toxin type A.

3. The method of claim 1, wherein the botulinum toxin is botulinum toxin type B.

4. The method of claim 1, wherein the method of local administration is injection.

5. The method of claim 1, wherein the administering is by non-intramuscular injection.

6. The method of claim 1, wherein the administering is subdermal, intradermal or transdermal.

7. The method of claim 1, wherein the trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve and a greater occipital nerve.

8. A method for reducing the occurrence of a symptom of anxiety disorder in a patient with anxiety disorder, the method comprising locally administering a therapeutically effective amount of a botulinum toxin non-intramuscularly to a trigeminal sensory nerve or to the vicinity of a trigeminal sensory nerve of the patient, thereby reducing the occurrence of a symptom of anxiety disorder, wherein the administering is subdermal, intradermal or transdermal.

9. The method of claim 8, wherein the botulinum toxin is botulinum toxin type A.

10. The method of claim 8, wherein the botulinum toxin is botulinum toxin type B.

11. The method of claim 8, wherein the method of local administration is injection.

12. The method of claim 8, wherein the administering is by non-intramuscular injection.

13. The method of claim 8, wherein the administering is subdermal.

14. The method of claim 8, wherein the therapeutically effective amount of the botulinum toxin administered is between about 1 unit and about 3,000 units.

15. The method of claim 8, wherein the trigeminal sensory nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve and a greater occipital nerve.

16. A method for treating bipolar disorder in a patient in need thereof, comprising locally administering a botulinum toxin non-intramuscularly to a trigeminal nerve of the patient, thereby treating the bipolar disorder, wherein the administering is subdermal, intradermal or transdermal.

17. The method of claim 16, wherein the botulinum toxin is botulinum toxin type A.

18. The method of claim 16, wherein the method of local administration is injection.

19. The method of claim 16, wherein the botulinum toxin is botulinum toxin type B.

20. The method of claim 16, wherein the trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve and a greater occipital nerve.

\* \* \* \* \*